US012171952B2

(12) United States Patent
O'Keefe et al.

(10) Patent No.: US 12,171,952 B2
(45) Date of Patent: *Dec. 24, 2024

(54) MEDICAL TUBE CLEARANCE DEVICE

(71) Applicant: CLEARFLOW, INC., Irvine, CA (US)

(72) Inventors: Kathryn Bernadine O'Keefe, Bend, OR (US); Stephen Riddle McDaniel, San Francisco, CA (US); Edward M. Boyle, Jr., Bend, OR (US); Kenneth Allan Beres, Studio City, CA (US); Matthew Christopher Barra, Leominster, MA (US); Thomas Urbanik, Somerville, MA (US); Chelsea Ann Gammon, San Diego, CA (US); Kenneth J. Chesnin, Long Beach, CA (US)

(73) Assignee: CLEARFLOW, INC., Irvine, CA (US)

( * ) Notice: Subject to any disclaimer, the term of this patent is extended or adjusted under 35 U.S.C. 154(b) by 536 days.

This patent is subject to a terminal disclaimer.

(21) Appl. No.: 16/593,547

(22) Filed: Oct. 4, 2019

(65) Prior Publication Data
US 2020/0030502 A1 Jan. 30, 2020

Related U.S. Application Data

(63) Continuation of application No. 14/624,161, filed on Feb. 17, 2015, now Pat. No. 10,471,189.
(Continued)

(51) Int. Cl.
*A61M 25/00* (2006.01)
*A61M 1/00* (2006.01)

(52) U.S. Cl.
CPC ............... *A61M 25/00* (2013.01); *A61M 1/83* (2021.05); *A61M 1/84* (2021.05);
(Continued)

(58) Field of Classification Search
CPC .... A61M 1/00; A61M 1/0001; A61M 1/0011; A61M 1/60; A61M 1/62; A61M 1/604;
(Continued)

(56) References Cited

U.S. PATENT DOCUMENTS 3,416,532 A 12/1968 Richard et al.
3,946,741 A 3/1976 Adair
(Continued)

FOREIGN PATENT DOCUMENTS

CN 201768722 U 3/2011
CN 102772833 A 11/2012
(Continued)

OTHER PUBLICATIONS

Office action (and translation) issued in corresponding Japanese Patent Application No. 2016-569578 dated Dec. 12, 2018, 17 pages.
(Continued)

*Primary Examiner* — Kevin C Sirmons
*Assistant Examiner* — Alexandra Lalonde

(57) ABSTRACT

A device for clearing obstructions from a medical tube is disclosed. The device includes an enclosure having an interior and an exterior, the enclosure comprising a distal opening for providing access to the interior of the enclosure. The device further includes a spool provided within the enclosure that is rotatable about an axis and an elongated guide member coupled to the spool such that the rotation of the spool causes the elongated guide member to wind or unwind about the spool. The device further includes a drive mechanism that is operable to rotate the spool within the enclosure without compromising a sterile field within the enclosure.

22 Claims, 17 Drawing Sheets

Related U.S. Application Data

(60) Provisional application No. 61/940,713, filed on Feb. 17, 2014.

(52) U.S. Cl.
CPC .............. *A61M 2025/0008* (2013.01); *A61M 2025/0019* (2013.01); *A61M 2209/10* (2013.01)

(58) Field of Classification Search
CPC ............ A61M 1/64; A61M 1/65; A61M 1/66; A61M 1/67; A61M 1/68; A61M 1/682; A61M 1/684; A61M 1/98; A61M 1/982; A61M 1/984; A61M 1/985; A61M 1/0003; A61M 1/0023; A61M 1/71; A61M 1/72; A61M 1/73; A61M 1/732; A61M 1/734; A61M 1/74; A61M 1/741; A61M 1/76; A61M 1/7411; A61M 1/743; A61M 1/75; A61M 1/77; A61M 1/772; A61M 1/774; A61M 1/777; A61M 1/78; A61M 1/782; A61M 1/784; A61M 1/785; A61M 1/79; A61M 1/80; A61M 1/802; A61M 1/804; A61M 1/81; A61M 1/815; A61M 1/82; A61M 1/83; A61M 1/84; A61M 1/843; A61M 1/85; A61M 1/86; A61M 1/87; A61M 1/88; A61M 1/89; A61M 1/882; A61M 1/884; A61M 1/892; A61M 1/893; A61M 1/895; A61M 1/90; A61M 1/91; A61M 1/912; A61M 1/913; A61M 1/915; A61M 1/917; A61M 1/918; A61M 1/92; A61M 1/94; A61M 1/95; A61M 1/96; A61M 1/962; A61M 1/964; A61M 1/966; A61M 2025/0019; A61M 2025/0008; A61M 39/08; A61M 2039/082; A61M 2039/085; A61M 2039/087; A61M 2205/18; A61M 2209/10; A61M 5/00; A61M 5/001; A61M 25/00; A61M 25/0105; A61M 2205/33; A61M 2205/50; A61M 2205/502; A61M 2205/505; A61M 25/09; A61M 25/0941; A61M 25/0905; A61M 25/0127; A61M 25/0158; A61M 2025/09116; A61M 2205/8275; A61M 2205/8287; A61B 90/70; A61B 2090/701; A61B 2018/0097

See application file for complete search history.

(56) References Cited

U.S. PATENT DOCUMENTS

| | | | |
|---|---|---|---|
| 3,957,054 A | 5/1976 | McFarlane | |
| 3,991,762 A | 11/1976 | Radford | |
| 4,006,743 A | 2/1977 | Kowarski | |
| 4,056,104 A | 11/1977 | Jaffe | |
| 4,148,319 A | 4/1979 | Kasper et al. | |
| 4,160,451 A | 7/1979 | Chittenden | |
| 4,228,802 A | 10/1980 | Trott | |
| 4,257,422 A | 3/1981 | Duncan | |
| 4,317,452 A | 3/1982 | Russo et al. | |
| 4,324,262 A | 4/1982 | Hall | |
| 4,398,910 A | 8/1983 | Blake et al. | |
| 4,429,693 A | 2/1984 | Blake et al. | |
| 4,445,897 A | 5/1984 | Ekbladh et al. | |
| 4,465,481 A | 8/1984 | Blake | |
| 4,523,920 A | 6/1985 | Russo | |
| 4,546,519 A * | 10/1985 | Pembroke | A61B 1/122 15/104.33 |
| 4,569,344 A | 2/1986 | Palmer | |
| 4,628,928 A | 12/1986 | Lowell | |
| 4,638,539 A | 1/1987 | Palmer | |
| 4,692,153 A | 9/1987 | Berlin et al. | |
| 4,696,296 A | 9/1987 | Palmer | |
| 4,698,058 A | 10/1987 | Greenfeld et al. | |
| 4,706,671 A | 11/1987 | Weinrib | |
| 4,723,549 A | 2/1988 | Wholey et al. | |
| 4,728,319 A | 3/1988 | Masch | |
| 4,762,125 A | 8/1988 | Leiman et al. | |
| 4,771,772 A | 9/1988 | DeWitt | |
| 4,781,678 A | 11/1988 | de Couet et al. | |
| 4,865,030 A | 9/1989 | Polyak | |
| 4,865,586 A | 9/1989 | Hedberg | |
| 4,889,106 A | 12/1989 | Watanabe | |
| 4,909,781 A | 3/1990 | Husted | |
| 4,921,488 A | 5/1990 | Maitz et al. | |
| 4,950,232 A | 8/1990 | Ruzicka et al. | |
| 4,967,743 A | 11/1990 | Lambert | |
| 5,003,657 A | 4/1991 | Boiteau et al. | |
| 5,009,659 A | 4/1991 | Hamlin et al. | |
| 5,062,835 A | 11/1991 | Maitz et al. | |
| 5,073,164 A | 12/1991 | Hollister et al. | |
| 5,116,310 A | 5/1992 | Seder et al. | |
| D328,790 S | 8/1992 | Herweck et al. | |
| 5,141,503 A | 8/1992 | Sewell, Jr. | |
| 5,188,618 A | 2/1993 | Thomas | |
| 5,215,522 A | 6/1993 | Page et al. | |
| 5,240,675 A | 8/1993 | Wilk et al. | |
| D340,285 S | 10/1993 | Herweck et al. | |
| 5,251,356 A | 10/1993 | Daki et al. | |
| 5,260,020 A | 11/1993 | Wilk et al. | |
| 5,261,877 A | 11/1993 | Fine et al. | |
| 5,297,310 A | 3/1994 | Cox et al. | |
| 5,336,177 A | 8/1994 | Marcus | |
| 5,349,950 A | 9/1994 | Ulrich et al. | |
| 5,370,610 A | 12/1994 | Reynolds | |
| 5,490,503 A | 2/1996 | Hollister | |
| 5,505,713 A | 4/1996 | Van Antwerp | |
| 5,514,112 A | 5/1996 | Chu et al. | |
| 5,520,635 A | 5/1996 | Gelbfish | |
| 5,522,801 A | 6/1996 | Wang | |
| 5,536,242 A * | 7/1996 | Willard | A61B 17/32037 604/35 |
| 5,536,248 A | 7/1996 | Weaver et al. | |
| 5,538,511 A | 7/1996 | Van Antwerp | |
| 5,599,299 A | 2/1997 | Weaver et al. | |
| 5,599,300 A | 2/1997 | Weaver et al. | |
| 5,630,823 A | 5/1997 | Schmitz-Rode et al. | |
| 5,653,696 A | 8/1997 | Shiber | |
| 5,688,234 A | 11/1997 | Frisbie | |
| 5,693,011 A | 12/1997 | Onik | |
| 5,715,815 A | 2/1998 | Lorenzen et al. | |
| 5,768,741 A | 6/1998 | Leiman et al. | |
| 5,772,261 A | 6/1998 | Magram | |
| 5,788,678 A | 8/1998 | Van Antwerp | |
| 5,788,681 A | 8/1998 | Weaver et al. | |
| 5,788,710 A | 8/1998 | Bates et al. | |
| 5,807,330 A | 9/1998 | Teitelbaum | |
| 5,830,127 A | 11/1998 | DeCastro | |
| 5,843,028 A | 12/1998 | Weaver et al. | |
| 5,868,720 A | 2/1999 | Van Antwerp | |
| 5,895,398 A | 4/1999 | Wensel et al. | |
| 5,897,534 A | 4/1999 | Heim et al. | |
| 5,902,314 A | 5/1999 | Koch | |
| 5,911,710 A | 6/1999 | Barry et al. | |
| 5,911,734 A | 6/1999 | Tsugita et al. | |
| 5,913,852 A | 6/1999 | Magram | |
| 5,921,952 A | 7/1999 | Desmond, III et al. | |
| 5,928,218 A | 7/1999 | Gelbfish | |
| 5,931,821 A | 8/1999 | Weilbacher et al. | |
| 5,957,932 A | 9/1999 | Bates et al. | |
| 5,964,004 A | 10/1999 | Bean | |
| 5,964,223 A | 10/1999 | Baran | |
| 5,989,241 A | 11/1999 | Plishka et al. | |
| 6,045,623 A | 4/2000 | Cannon | |
| 6,080,170 A | 6/2000 | Nash et al. | |
| 6,082,361 A | 7/2000 | Morejon | |
| 6,129,697 A | 10/2000 | Drasler et al. | |
| 6,168,603 B1 | 1/2001 | Leslie et al. | |
| 6,183,450 B1 | 2/2001 | Lois | |
| 6,248,100 B1 | 6/2001 | de Toledo et al. | |

(56) References Cited

U.S. PATENT DOCUMENTS

| | | |
|---|---|---|
| 6,264,624 B1 | 7/2001 | Desmond, III et al. |
| 6,299,604 B1 | 10/2001 | Ragheb et al. |
| 6,383,196 B1 | 5/2002 | Leslie et al. |
| 6,436,112 B2 | 8/2002 | Wensel et al. |
| 6,454,775 B1 | 9/2002 | Demarais et al. |
| 6,485,497 B2 | 11/2002 | Wensel et al. |
| 6,494,208 B1 | 12/2002 | Morejon |
| 6,508,789 B1 | 1/2003 | Sinnott et al. |
| 6,514,273 B1 | 2/2003 | Voss et al. |
| 6,530,935 B2 | 3/2003 | Wensel et al. |
| 6,547,761 B2 | 4/2003 | Liu |
| 6,562,024 B2 | 5/2003 | Alvarez de Toledo et al. |
| 6,582,400 B1 | 6/2003 | Hawk et al. |
| 6,629,956 B1 | 10/2003 | Polidoro et al. |
| 6,638,253 B2 | 10/2003 | Breznock |
| 6,660,014 B2 | 12/2003 | Demarais et al. |
| 6,663,650 B2 | 12/2003 | Sepetka et al. |
| 6,679,262 B1 | 1/2004 | Morejon |
| 6,692,459 B2 | 2/2004 | Teitelbaum |
| 6,692,508 B2 | 2/2004 | Wensel et al. |
| 6,692,509 B2 | 2/2004 | Wensel et al. |
| 6,699,331 B1 | 3/2004 | Kritzler |
| 6,702,830 B1 | 3/2004 | Demarais et al. |
| 6,730,104 B1 | 5/2004 | Sepetka et al. |
| 6,740,096 B2 | 5/2004 | Teague et al. |
| 6,767,338 B2 | 7/2004 | Hawk et al. |
| 6,780,193 B2 | 8/2004 | Leslie et al. |
| 6,783,536 B2 | 8/2004 | Vilsmeier et al. |
| 6,824,545 B2 | 11/2004 | Sepetka et al. |
| 6,849,061 B2 | 2/2005 | Wagner |
| 6,866,657 B2 | 3/2005 | Shchervinsky |
| 6,889,400 B2 | 5/2005 | Kawazoe et al. |
| 6,893,418 B2 | 5/2005 | Liu |
| 6,893,424 B2 | 5/2005 | Shchervinsky |
| 6,902,550 B2 | 6/2005 | Want et al. |
| 6,905,484 B2 | 6/2005 | Buckman et al. |
| 6,920,662 B2 | 7/2005 | Moore |
| 6,945,977 B2 | 9/2005 | Demarais et al. |
| 7,004,954 B1 | 2/2006 | Voss et al. |
| 7,028,707 B2 | 4/2006 | Corbeil et al. |
| 7,037,313 B2 | 5/2006 | Ahn et al. |
| 7,101,380 B2 | 9/2006 | Khachin et al. |
| 7,125,402 B1 | 10/2006 | Yarger |
| 7,135,010 B2 | 11/2006 | Buckman et al. |
| 7,141,038 B2 | 11/2006 | Whalen et al. |
| 7,211,067 B2 | 5/2007 | Hawk et al. |
| 7,229,433 B2 | 6/2007 | Mullen |
| 7,241,287 B2 | 7/2007 | Shehada et al. |
| 7,241,299 B2 | 7/2007 | Gerard |
| 7,244,251 B2 | 7/2007 | Shehada et al. |
| 7,252,659 B2 | 8/2007 | Shehada et al. |
| 7,264,616 B2 | 9/2007 | Shehada et al. |
| 7,267,671 B2 | 9/2007 | Shehada |
| 7,285,126 B2 | 10/2007 | Sepetka et al. |
| 7,326,197 B2 | 2/2008 | Breznock et al. |
| 7,338,478 B2 | 3/2008 | Leiboff |
| 7,338,501 B2 | 3/2008 | Teague et al. |
| 7,419,483 B2 | 9/2008 | Shehada |
| 7,610,106 B2 | 10/2009 | Yacoubian |
| 7,686,801 B2 | 3/2010 | Corbeil et al. |
| 7,695,467 B2 | 4/2010 | Breznock et al. |
| 7,780,639 B2 | 8/2010 | Van Lue |
| 7,799,046 B2 | 9/2010 | White et al. |
| 7,811,293 B2 | 10/2010 | Simpson et al. |
| 7,854,728 B2 | 12/2010 | Boyle |
| 7,867,241 B2 | 1/2011 | Brock et al. |
| 7,951,243 B2 | 5/2011 | Boyle, Jr. et al. |
| 7,992,561 B2 | 8/2011 | Baker, Jr. et al. |
| 8,048,233 B2 | 11/2011 | Boyle, Jr. et al. |
| 8,157,919 B2 | 4/2012 | Vazales et al. |
| 8,246,752 B2 | 8/2012 | Boyle, Jr. |
| 8,262,645 B2 | 9/2012 | Bagwell et al. |
| 8,388,759 B2 | 3/2013 | Boyle, Jr. et al. |
| 8,566,995 B2 | 10/2013 | Asano et al. |
| 10,471,189 B2* | 11/2019 | O'Keefe ............ A61M 1/83 |
| 2001/0018572 A1 | 8/2001 | Kinsey et al. |
| 2002/0058915 A1 | 5/2002 | Wakabayashi |
| 2002/0128601 A1 | 9/2002 | Reilly et al. |
| 2003/0069551 A1 | 4/2003 | Bradley, III et al. |
| 2003/0181876 A1 | 9/2003 | Ahn et al. |
| 2003/0216760 A1 | 11/2003 | Welch et al. |
| 2004/0006331 A1 | 1/2004 | Shchervinsky |
| 2004/0073243 A1 | 4/2004 | Sepetka et al. |
| 2004/0078026 A1 | 4/2004 | Wagner |
| 2004/0092956 A1 | 5/2004 | Liddicoat et al. |
| 2004/0181191 A1 | 9/2004 | Teitelbaum |
| 2004/0219028 A1 | 11/2004 | Demarais et al. |
| 2004/0230132 A1 | 11/2004 | Shehada |
| 2005/0004514 A1* | 1/2005 | Hochman ............ A61M 5/1456 604/67 |
| 2005/0033348 A1 | 2/2005 | Sepetka et al. |
| 2005/0055033 A1 | 3/2005 | Leslie et al. |
| 2005/0059995 A1 | 3/2005 | Sepetka et al. |
| 2005/0085849 A1 | 4/2005 | Sepetka et al. |
| 2005/0125024 A1 | 6/2005 | Sepetka et al. |
| 2005/0154373 A1 | 7/2005 | Deutsch |
| 2005/0171478 A1 | 8/2005 | Selmon et al. |
| 2005/0171566 A1 | 8/2005 | Kanamaru |
| 2005/0216030 A1 | 9/2005 | Sepetka et al. |
| 2005/0216050 A1 | 9/2005 | Sepetka et al. |
| 2005/0228363 A1 | 10/2005 | Leiboff |
| 2005/0228417 A1 | 10/2005 | Teitelbaum et al. |
| 2005/0288686 A1 | 12/2005 | Sepetka et al. |
| 2006/0004404 A1 | 1/2006 | Khachin et al. |
| 2006/0142697 A1 | 6/2006 | Hawk et al. |
| 2006/0167416 A1 | 7/2006 | Mathis et al. |
| 2006/0184154 A1* | 8/2006 | Moberg ............ A61M 5/16854 604/151 |
| 2006/0195069 A1 | 8/2006 | Opie et al. |
| 2006/0195137 A1 | 8/2006 | Sepetka et al. |
| 2006/0206097 A1 | 9/2006 | Breznock |
| 2006/0264974 A1 | 11/2006 | Khachin et al. |
| 2006/0264988 A1 | 11/2006 | Boyle |
| 2006/0276814 A1 | 12/2006 | Omata et al. |
| 2007/0032779 A1 | 2/2007 | Accisano et al. |
| 2007/0049904 A1 | 3/2007 | Deutsch |
| 2007/0078389 A1 | 4/2007 | Whalen et al. |
| 2007/0083189 A1 | 4/2007 | Lampropoulos et al. |
| 2007/0135795 A1 | 6/2007 | De Paulis |
| 2007/0149946 A1 | 6/2007 | Viswanathan et al. |
| 2007/0179513 A1 | 8/2007 | Deutsch |
| 2007/0198030 A1 | 8/2007 | Martin et al. |
| 2007/0208300 A1 | 9/2007 | Pravong et al. |
| 2007/0208371 A1 | 9/2007 | French et al. |
| 2007/0288036 A1 | 12/2007 | Seshadri et al. |
| 2008/0045881 A1 | 2/2008 | Teitelbaum et al. |
| 2008/0051720 A1 | 2/2008 | Nash et al. |
| 2008/0091146 A1 | 4/2008 | Solovay et al. |
| 2008/0109032 A1 | 5/2008 | Sepetka et al. |
| 2008/0119869 A1 | 5/2008 | Teague et al. |
| 2008/0177276 A1 | 7/2008 | Teague et al. |
| 2008/0177296 A1 | 7/2008 | Sepetka et al. |
| 2008/0183197 A1 | 7/2008 | Sepetka et al. |
| 2008/0183198 A1 | 7/2008 | Sepetka et al. |
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0215077 A1 | 9/2008 | Sepetka et al. |
| 2008/0234706 A1 | 9/2008 | Sepetka et al. |
| 2009/0000045 A1 | 1/2009 | Kanno et al. |
| 2009/0030402 A1* | 1/2009 | Adahan ................ A61M 1/964 15/300.1 |
| 2009/0062772 A1 | 3/2009 | Wakeford et al. |
| 2009/0157060 A1 | 6/2009 | Teague et al. |
| 2009/0188531 A1 | 7/2009 | Boyle, Jr. et al. |
| 2009/0264833 A1* | 10/2009 | Boyle, Jr. ............ A61B 90/70 604/257 |
| 2009/0326513 A1 | 12/2009 | Deutsch et al. |
| 2010/0174290 A1 | 7/2010 | Wuebbeling et al. |
| 2011/0023888 A1 | 2/2011 | Vazales et al. |
| 2011/0040285 A1 | 2/2011 | Boyle |
| 2011/0098660 A1 | 4/2011 | Porreca, Jr. |
| 2011/0106019 A1 | 5/2011 | Bagwell et al. |
| 2011/0289705 A1 | 12/2011 | Asano et al. |

(56) References Cited

U.S. PATENT DOCUMENTS

| | | | |
|---|---|---|---|
| 2012/0285485 A1* | 11/2012 | Majeed | B08B 9/0436 134/8 |
| 2013/0018304 A1 | 1/2013 | Bagwell et al. | |
| 2013/0018305 A1 | 1/2013 | Bagwell et al. | |
| 2013/0018331 A1 | 1/2013 | Bagwell et al. | |
| 2013/0104884 A1 | 5/2013 | Vazales et al. | |
| 2013/0237930 A1* | 9/2013 | Mulvihill | A61M 25/0082 604/264 |
| 2014/0150782 A1 | 6/2014 | Vazales et al. | |
| 2014/0323906 A1* | 10/2014 | Peatfield | A61M 1/84 600/561 |
| 2015/0202414 A1 | 7/2015 | Hwang | |
| 2015/0305819 A1 | 10/2015 | Krause | |
| 2016/0175563 A1 | 6/2016 | Woehr et al. | |

FOREIGN PATENT DOCUMENTS

| | | |
|---|---|---|
| DE | 202009006908 U1 | 11/2010 |
| JP | S61033282 | 2/1986 |
| JP | H08275918 A | 10/1996 |
| JP | 2004208961 | 7/2004 |
| WO | WO1994003226 A1 | 2/1994 |
| WO | WO2004098654 A2 | 11/2004 |
| WO | WO2004108051 A2 | 12/2004 |
| WO | WO2005067647 A2 | 7/2005 |
| WO | WO2006071855 A2 | 7/2006 |
| WO | WO2006074283 A2 | 7/2006 |
| WO | WO2007090057 A2 | 8/2007 |
| WO | WO2007098376 A2 | 8/2007 |
| WO | WO2008059647 A1 | 5/2008 |
| WO | WO2010021775 A1 | 2/2010 |
| WO | WO2011061544 A1 | 5/2011 |

OTHER PUBLICATIONS

European Supplementary Partial Search Report issued in corresponding European Patent Application No. EP 15749639, dated Oct. 17, 2017, 13 pages.

International Search Report issued in corresponding International Patent Application No. PCT/US2018/017807 dated Apr. 26, 2018, 3 pages.

Office action issued in corresponding Canadian Patent Application No. 2,939,624 dated Dec. 10, 2021, 5 pages.

Office action issued in corresponding Japanese Patent Application No. 2021-171626 dated Aug. 30, 2022, 9 pages (with translatoin).

Office action issued in corresponding Chinese Patent Application No. 202110906358.0 dated Dec. 20, 2022, 16 pages (with translation).

* cited by examiner

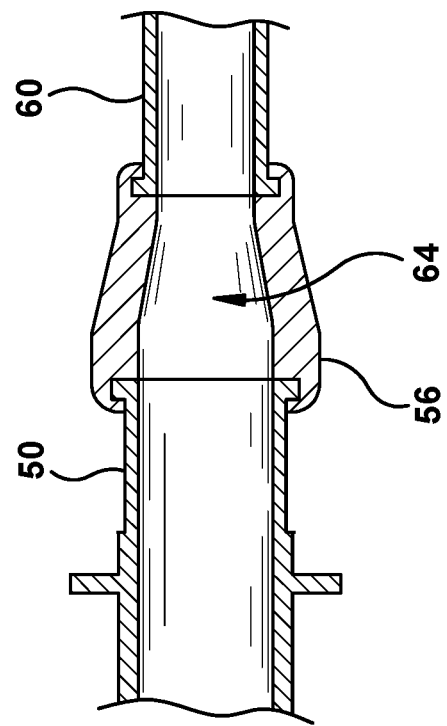
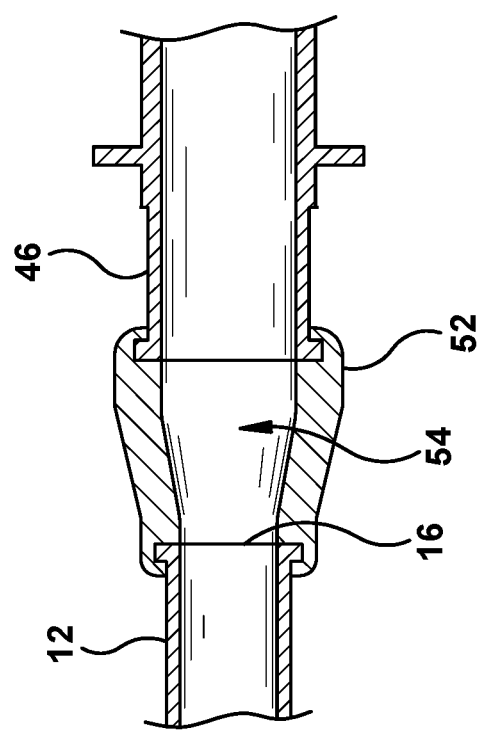

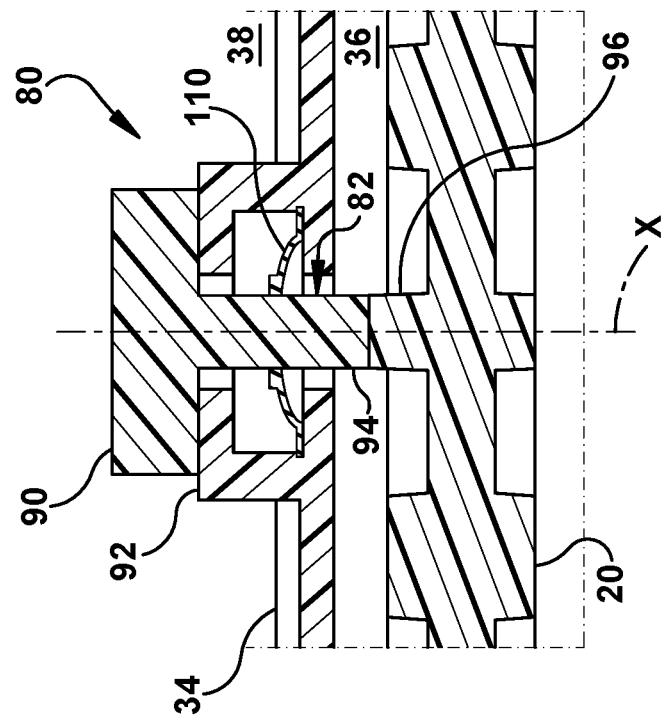
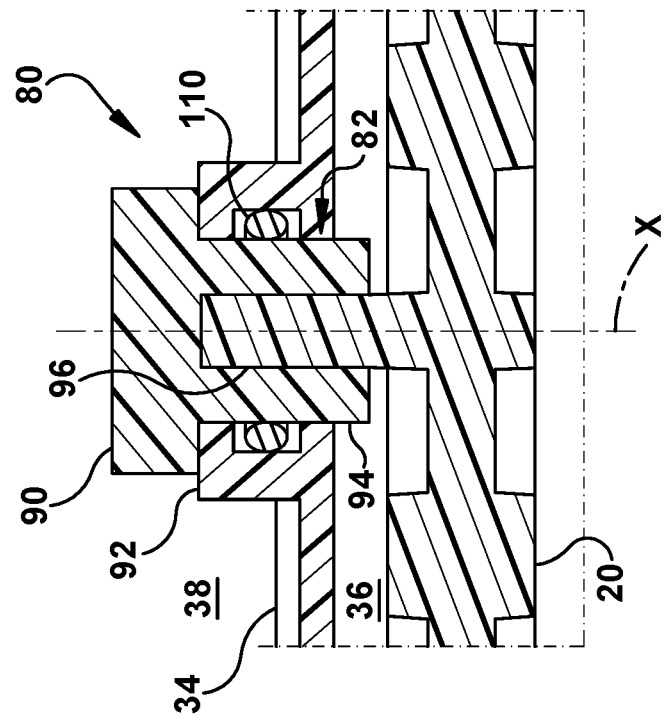

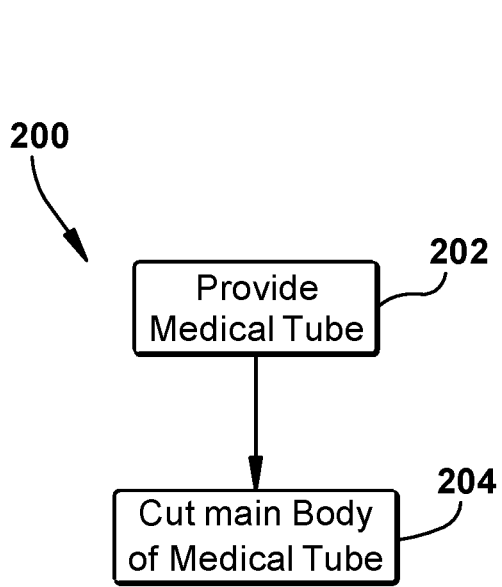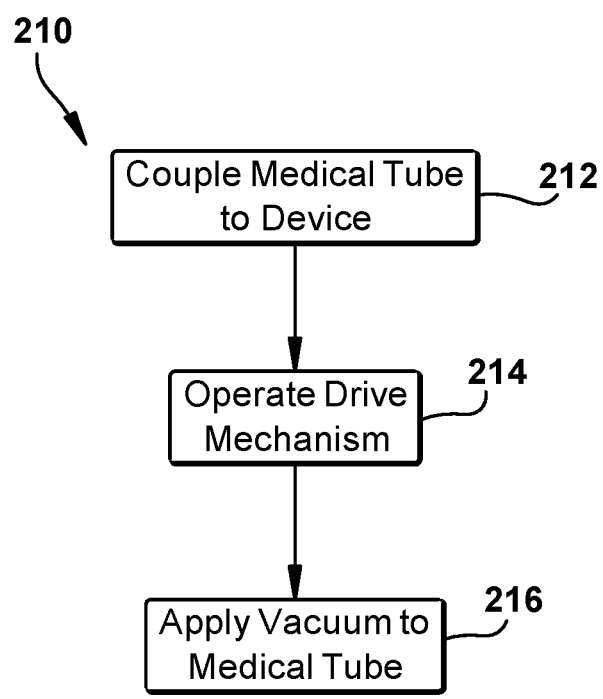
Fig. 26
Fig. 27

MEDICAL TUBE CLEARANCE DEVICE

CROSS-REFERENCE TO RELATED APPLICATIONS

This application claims the benefit of U.S. patent application Ser. No. 14/624,161, filed Feb. 17, 2015, which claims the benefit of U.S. Provisional Application No. 61/940,713, filed Feb. 17, 2014, which are incorporated in its entirety herein by reference.

TECHNICAL FIELD

This application relates generally to a medical tube assembly and, more specifically, to a device for clearing obstructions from a medical tube of the medical tube assembly.

BACKGROUND

Medical tubes can be used to deliver fluids or devices into a body and/or drain bodily fluids and secretions from compartments and structures within the body. For example, medical tubes can be used to drain fluid from one's bladder, from the colon or other portions of the alimentary tract, or from the lungs or other organs in conjunction with various therapies. As another example, medical tubes can be used to drain blood and other fluids that typically accumulate within the body cavity following traumatic surgery. As yet another example, medical tubes can be used to deliver fluids to a body for nourishment or they can be used to provide access to the vasculature for removal or delivery of fluids or devices. Typically, a medical tube is inserted into the patient so that its distal end is provided in or adjacent the space where it is desired to remove or deliver material while a proximal portion remains outside the patient's body, where it can be connected, for example, to a suction source.

Fluids passing through a medical tube (particularly those including blood or blood platelets) can form clots or other obstructions within the medical tube, which can partially or totally obstruct the suction pathway within the tube. Obstruction of the medical tube can impact its effectiveness to remove or deliver the fluid and other material for which it was originally placed, eventually rendering the medical tube partially or totally non-functional. In some cases, a non-functional tube can have serious or potentially life-threatening consequences. For example, if there is a blockage in a chest tube following cardiac or pulmonary surgery, the resulting accumulation of fluid around the heart and lungs without adequate drainage can cause serious adverse events such as pericardial tamponade and pneumothorax.

SUMMARY

The following presents a simplified summary of the disclosure in order to provide a basic understanding of some example aspects described in the detailed description.

In accordance with a first aspect, a device for clearing obstructions from a medical tube comprises an enclosure having an interior and an exterior, the enclosure comprising a distal opening for providing access to the interior of the enclosure. The device further comprises a spool provided within the enclosure that is rotatable about an axis and an elongated guide member coupled to the spool such that rotation of the spool causes the guide member to wind or unwind about the spool. The device further comprises a drive mechanism that is operable to rotate the spool within the enclosure without compromising a sterile field within the enclosure.

In accordance with a second aspect, a medical tube configured to be coupled to a clearance device that is operable to move a clearance member of the clearance device between a fully advanced state within the medical tube and retracted state comprises a main body and at least one pair of associated markings arranged on the main body such that cutting the main body at each of the associated markings will produce a cut tube portion with a distal end and a proximal end, the cut tube portion being configured such that when the cut tube portion is coupled with the clearance device and the clearance member is moved within the cut tube portion to the fully advanced state, the clearance member will be advanced to a predetermined or user-selected location within the cut tube portion.

In accordance with a third aspect, an assembly comprises a medical tube and an indicator device that is configured to be aligned with the medical tube to indicate at least one pair of locations to cut the medical tube. Cutting the medical tube at a particular pair of such locations will produce a cut tube portion with a distal end and a proximal end, the cut tube portion being configured such that when coupled with a particular clearance device operable to move a clearance member from a retracted state to a fully advanced state within the cut tube portion, the clearance member will be disposed at a predetermined or user-selected location within the cut tube portion in the fully advanced state.

BRIEF DESCRIPTION OF THE DRAWINGS

Embodiments of the invention are better understood when the following detailed description is read with reference to the accompanying drawings, in which:

FIG. 6 is a cross-sectional view of the device coupled to the medical tube with an example medical tube connector;

FIG. 7 is a cross-sectional view of the device coupled to a discharge tube with an example discharge connector;

FIG. 10 is a cross-sectional view of a drive mechanism of the device according to one example configuration;

FIG. 11 is a cross-sectional view of the drive mechanism of the device according to another example configuration;

FIG. 26 is a flow chart illustrating steps of a method of calibrating a medical tube; and FIG. 27 is a flow chart illustrating steps of a method of clearing obstructions from a medical tube using a device for clearing obstructions from the medical tube.

DETAILED DESCRIPTION

Figure 1:
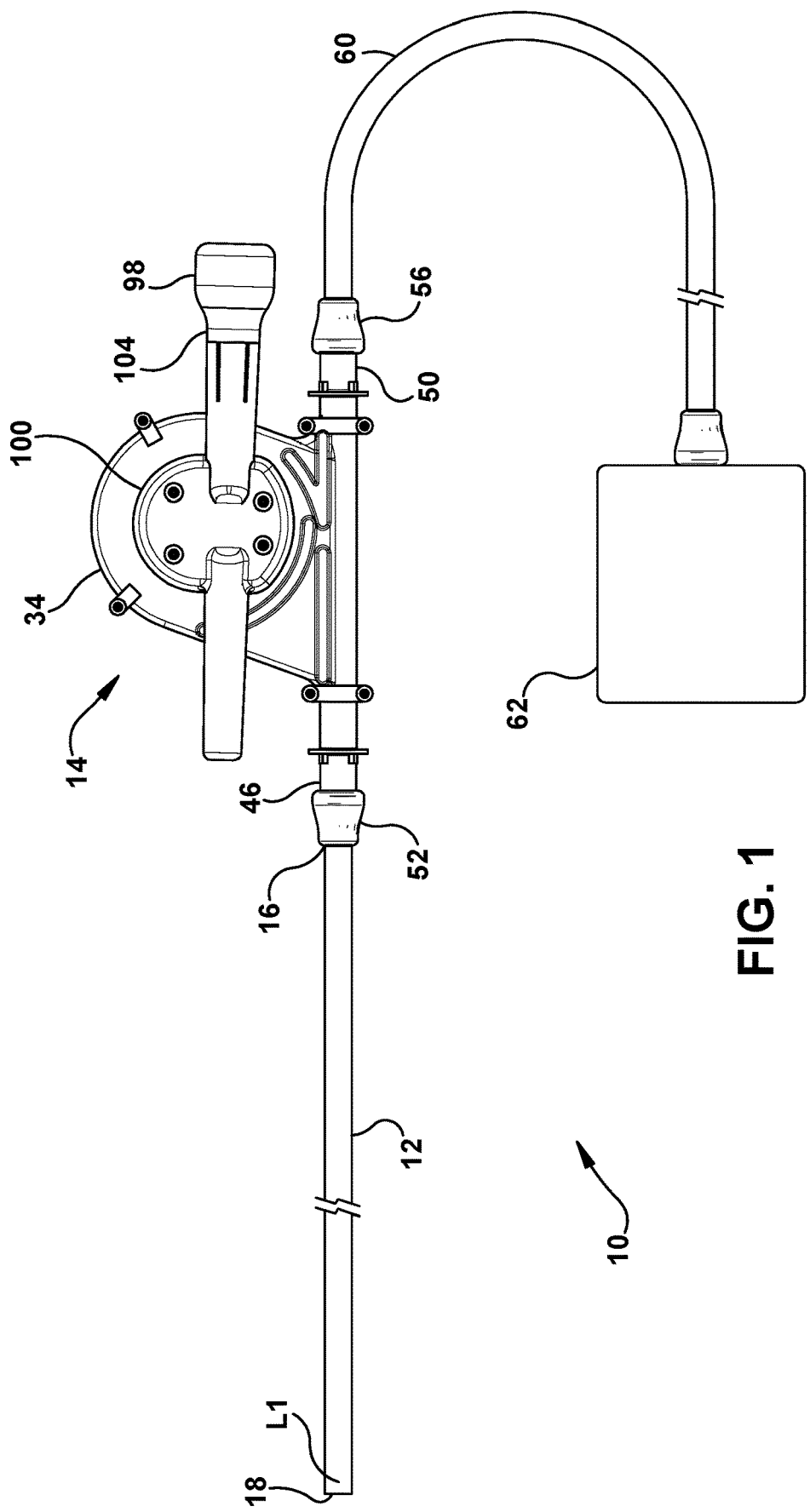
FIG. 1 is a schematic view of a medical tube assembly.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is to be noted that the terms "proximal" and "distal" as used herein when describing two ends or portions of a feature indicate a relative positioning that those two ends or portions will generally have along an in-line system that is tied to a patient, the distal end or portion being closer to the patient than the proximal end or portion. For example, in an in-line system comprising a widget that draws fluid from the patient through the widget along a flow path, a distal end or portion of a widget will be closer to a patient than a proximal end or portion of the widget along the flow path of the fluid.

Examples will now be described more fully hereinafter with reference to the accompanying drawings in which example embodiments are shown. Whenever possible, the same reference numerals are used throughout the drawings to refer to the same or like parts. However, aspects may be embodied in many different forms and should not be construed as limited to the embodiments set forth herein.

As shown in FIG. 1, a medical tube assembly 10 can comprise a medical tube 12 and a device 14 for clearing obstructions from a medical tube 12. The medical tube 12 can be a tube having a length, an inner diameter, and an outer diameter that can each vary between different embodiments. Indeed, the medical tube 12 can have a variety of different shapes and configurations without departing from the scope of the invention. The medical tube 12 can be used to drain bodily fluids and secretions from within body compartments and structures such as, for example, fluid from within a person's bladder, colon, lungs, brain, thoracic cavity, or any other body structure. The medical tube 12 can alternatively be used to deliver fluids or devices to a body compartment or structure. In some examples, the medical tube 12 can be used to drain bodily fluids and secretions from within body compartments and structures and deliver the fluids to other body compartments and structures.

The medical tube 12 can comprise a proximal opening 16 and a distal opening 18 and can be inserted into a patient so that its distal opening 18 is provided in or adjacent the space where it is desired to remove or deliver material while the proximal opening 16 remains outside the patient's body. In the example shown in FIG. 1, the proximal opening 16 and distal opening 18 respectively coincide with a proximal and distal end of the medical tube 12. However, in some examples, the proximal opening 16 and/or distal opening 18 may be openings along the medical tube 12 that are intermediate its ends.

Turning to FIGS. 2-5, the device 14 can comprise a spool 20 that is rotatable about an axis X and an elongated guide member 22 which, as will be discussed in further detail below, can be advanced or withdrawn through the medical tube 12 to help dislodge and/or draw obstructing material within the medical tube 12 without compromising a sterile field within the medical tube 12.

Figure 2:
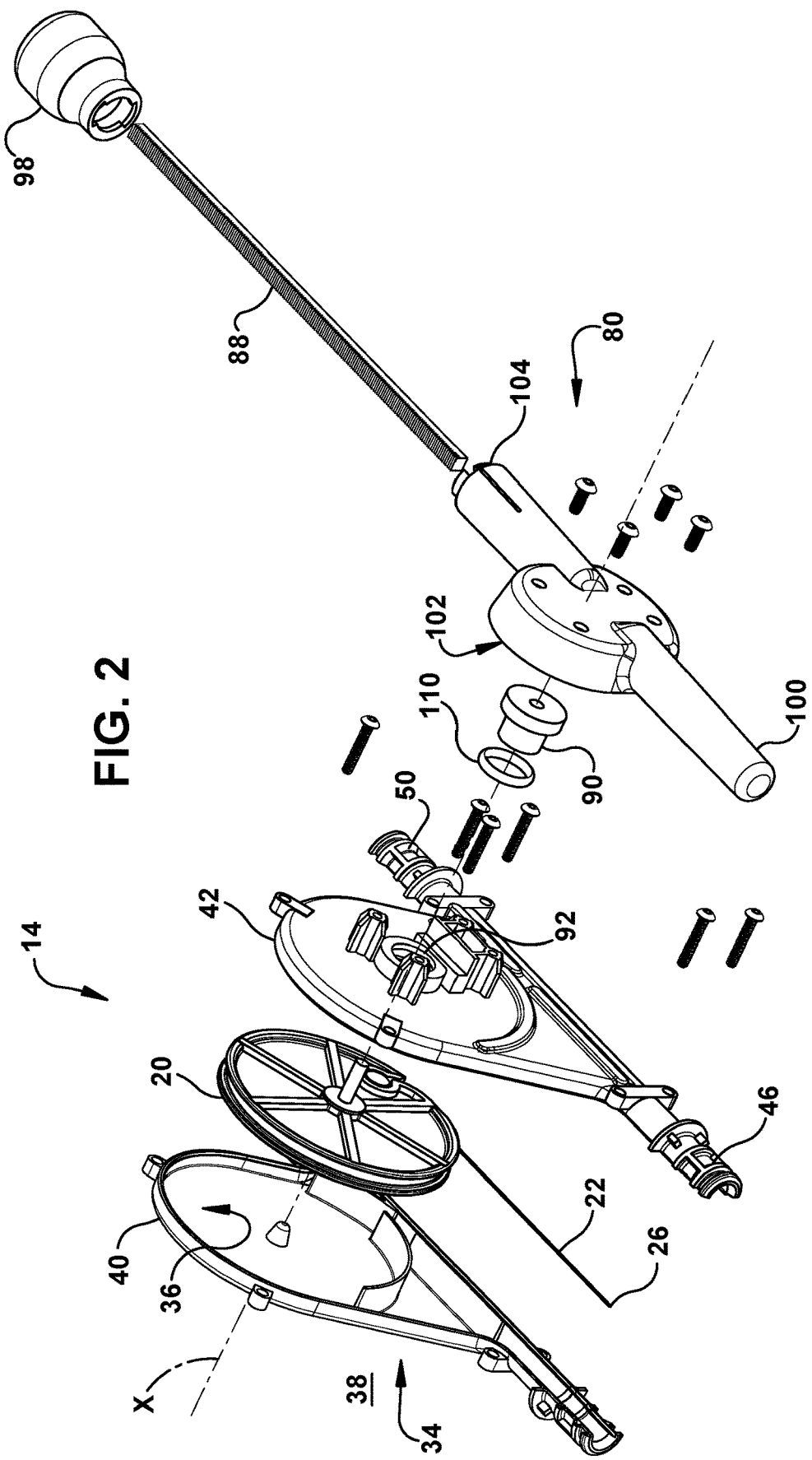
FIG. 2 is an exploded view of a device for clearing obstructions from a medical tube of the medical tube assembly.
Figure 3:
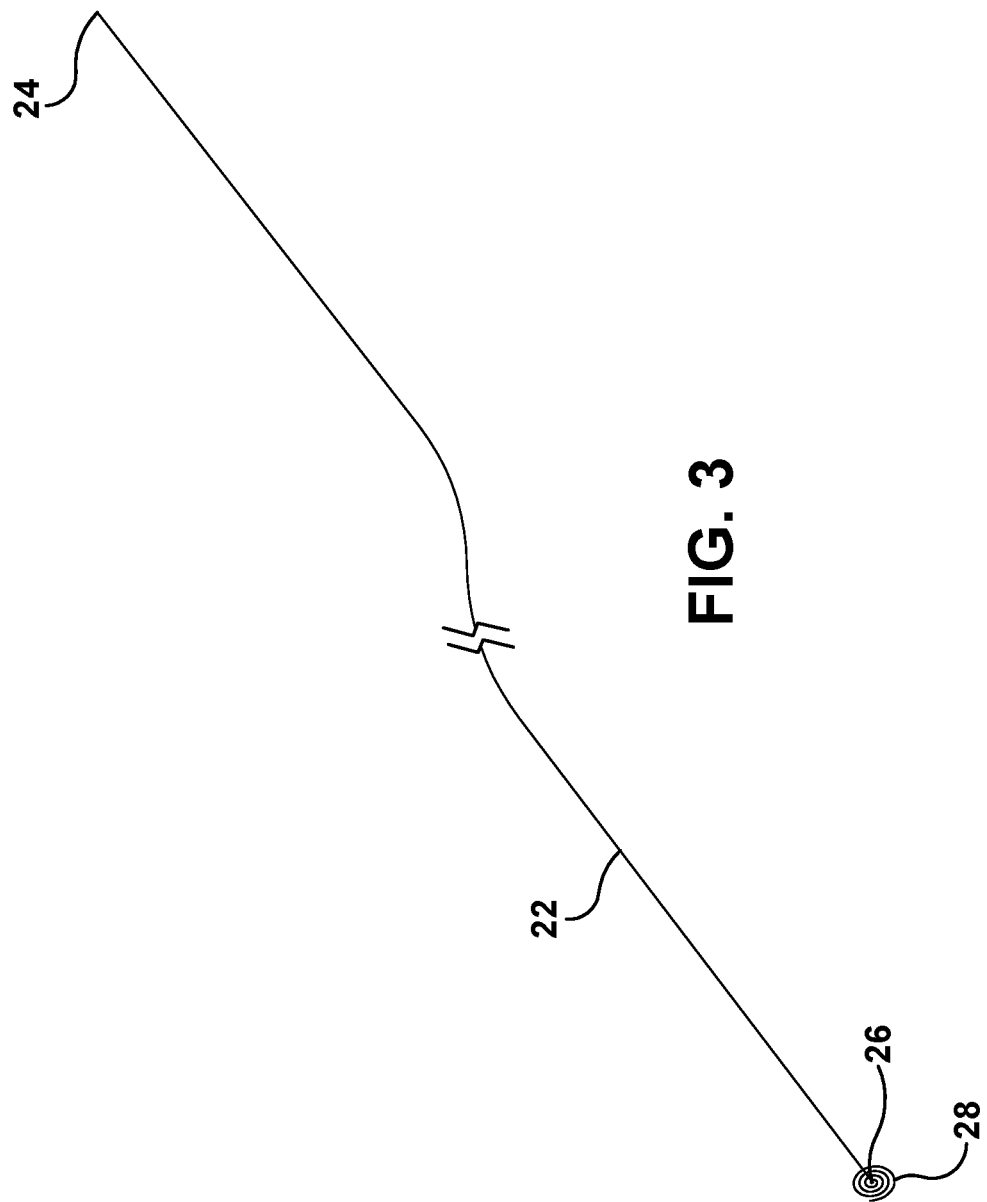
FIG. 3 is a perspective view of an example guide member and clearance member of the device.
Figure 5:
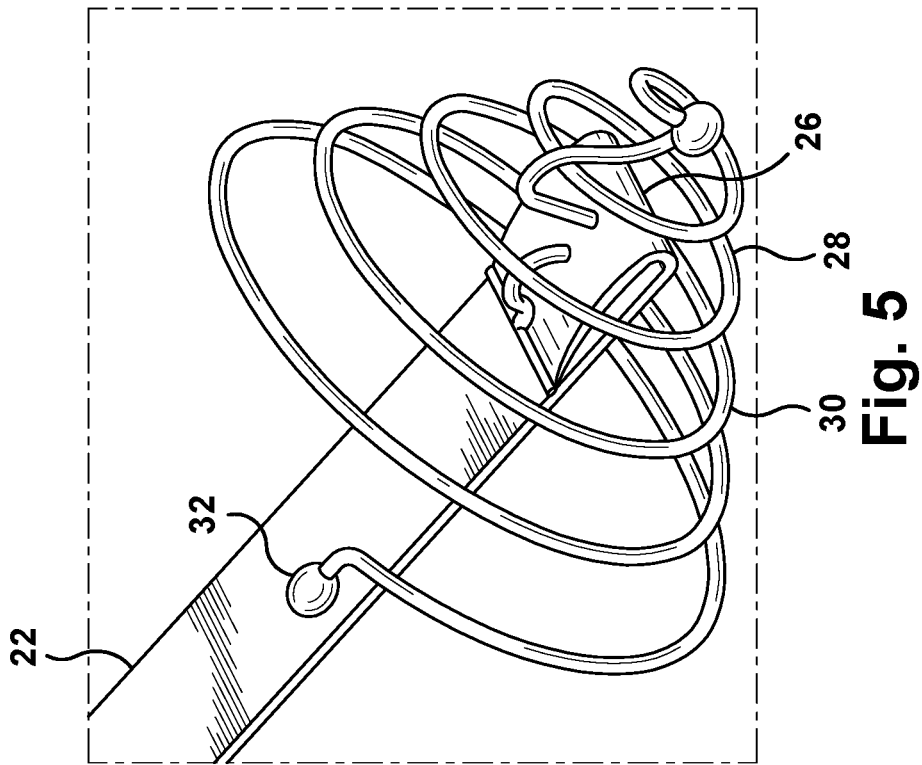
FIG. 5 is a perspective view of the guide member and clearance member shown in FIG. 4 in a reverse configuration.
Figure 4:
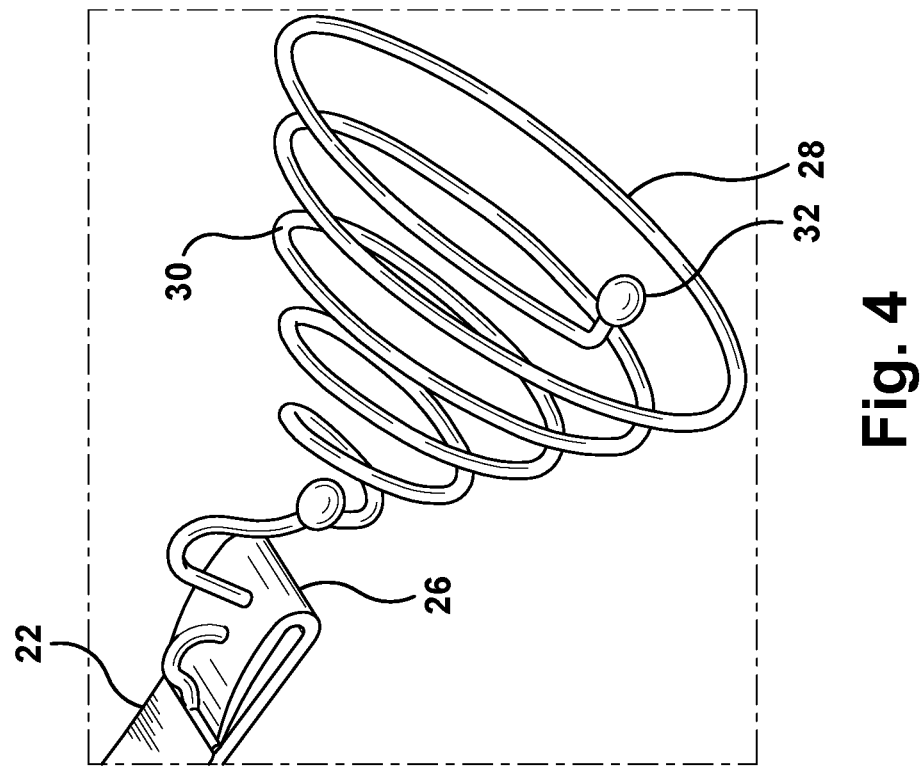
FIG. 4 is a perspective view of another example guide member and clearance member of the device.

In some examples, the guide member 22 can comprise a wire having a substantially circular cross-section (as shown in FIGS. 2 & 3) while in other examples, the guide member 22 can comprise a flat tape having a substantially rectangular cross-section (as shown in FIGS. 4 & 5). The guide member 22 can comprise a proximal end 24 and a distal end 26. The proximal end 24 of the guide member 22 can be coupled to the spool 20. Moreover, in some embodiments, the device 14 can comprise one or more clearance members 28 that can be coupled to the distal end 26 or other portions of the guide member 22. It is to be noted that the term "coupled" as used herein when describing two or more features means that the features can be integral with each other or that the features can be separate features that are removably or non-removably attached to each other using various means such as threads, fasteners, hooks, clips, adhesive, welds, or other means of attaching two separate features. For example, in some embodiments, the coupled guide member 22 and clearance member 28 may be integral components formed together of a single piece of wire, while the coupled guide member 22 and spool 20 may be separately attached features.

When the guide member 22 is coupled to the clearance member 28 and inserted within the medical tube 12, the guide member 22 can guide the clearance member 28 through the medical tube 12 as the guide member 22 is advanced or withdrawn through the medical tube 12. The clearance member 28 can be configured such that as the clearance member 28 is guided through the medical tube 12 by the guide member 22, the clearance member 28 can help dislodge and/or draw obstructing material within the medical tube 12. For example, the clearance member 28 can comprise a wire 30 comprising a plurality of coils arranged in a spiral configuration, as shown in FIGS. 4 & 5. The wire 30 can comprise a material with elastic or shape memory properties such as, for example, nickel-titanium that allows the plurality of coils to expand or conform to various shapes and sizes of the medical tube 12. Moreover, depending on which direction the clearance member 28 is being translated through the medical tube 12, the plurality of coils can reverse their conformation to produce substantially conical configurations of coils facing opposite directions, thereby reducing the resistance exerted on the clearance member 28 by the walls of the medical tube 12. If the medical tube 12 comprises any fluid intake apertures in its side walls, the wire 30 can comprise an end portion 32 that is sized or otherwise configured so that the end portion 32 will not fit through such apertures and potentially extend laterally out of the medical tube 12.

In other examples, the wire 30 of the clearance member 28 may comprise a loop or other structure that presents substantially no impediment to flow through the medical tube 12 past the clearance member 28 regardless of whether the clearance member 28 is at rest or being actuated within the medical tube 12. In a further embodiment, the clearance member 28 can comprise a brush with a plurality of bristles rather than the wire 30. The clearance member 28 can comprise any member that is translatable through the medical tube 12 to dislodge and/or draw obstructing material accumulated within the medical tube 12.

The guide member 22 can be coupled to the spool 20 such that rotation of the spool 20 about the axis X causes the guide member 22 to wind or unwind about the spool 20 and move between an advanced state and a retracted state. In some embodiments, the distal end 26 of the guide member 22 may be positioned within the medical tube 12 and coupled to the clearance member 28. If the spool 20 is rotated in one direction, the guide member 22 will wind about the spool 20, causing the guide member 22 and the coupled clearance member 28 to translate away from the distal opening 18 of the medical tube 12 (i.e., retract). Alternatively, if the spool 20 is rotated in the opposite direction, the guide member 22 will unwind about the spool 20, causing the guide member 22 and the coupled clearance member 28 to translate toward the distal opening 18 of the medical tube 12 (i.e., advance). Thus, rotation of the spool 20 can control the position and operation (actuation) of the guide member 22 and coupled clearance member 28 within the medical tube 12.

The guide member 22 can comprise a material with elastic or shape memory properties such as, for example, nickel-titanium that allows the guide member 22 to conform to the curvature of the spool 20 when wound about the spool 20 and also allows the guide member 22 take on or resume a more linear shape or configuration when advancing through the medical tube 12. Preferably, the guide member 22 comprises a material that is rigid enough to advance the clearance member 28 through the medical tube 12 when coupled to thereto. However, the guide member 22 may comprise a variety of different shapes, sizes and materials without departing from the scope of the invention.

In some embodiments, one or both of the clearance member 28 and the guide member 22 can be coated with at least one of a pharmacologic material, an anti-thrombogenic material, and an anti-infective material to assist in treating materials inside the medical tube 12.

As shown in FIGS. 2, the device 14 can comprise an enclosure 34 having an interior 36 and an exterior 38. The spool 20 and at least a portion of the guide member 22 can be provided within the interior 36 of the enclosure 34. The device 14 can be configured such that the enclosure 34 can be coupled with the medical tube 12 and the spool 20 can be rotated to advance or retract the guide member 22 within the medical tube 12 without compromising a sterile field within the medical tube 12 and the interior 36 of the enclosure 34.

More specifically, the enclosure 34 can comprise a first half portion 40 and a second half portion 42 that are coupled together. For example, the first and second half portions 40, 42 can be separate portions that are attached to each other using threaded fasteners or other attaching means to form a hermetical seal therebetween. The enclosure 34 can further comprise one or more opening portions for providing access to the interior 36 of the enclosure 34. For example, the enclosure 34 can comprise a distal opening 46 and in some examples, the enclosure 34 can also comprise a proximal opening 50 for providing access to the interior 36 of the enclosure 34.

In some examples, the device 14 can comprise one or more connectors to couple the opening portions of the enclosure 34 to the medical tube 12 or other structure and form a closed passageway therebetween. It to be noted that the phrase "closed passageway" as used herein is meant to describe a passageway that is not exposed to an exterior environment between its inlet and outlet, thereby preserving a sterile field that may be present within the passageway. For instance, as shown in FIGS. 1 & 6, the device 14 can comprise a medical tube connector 52. The medical tube connector 52 can be coupled to the distal opening 46 of the enclosure 34 and is removably coupleable to the medical tube 12 to form a first closed passageway 54 for fluid communication between the enclosure 34 and the medical tube 12 through the medical tube connector 52. The device 14 can also comprise a drainage connector 56, as shown in FIGS. 1 & 7. The drainage connector 56 can be coupled to the proximal opening 50 of the enclosure 34 and is removably coupleable to drainage structure such as, for example, a drainage tube 60 of the medical tube assembly 10, to form a second closed passageway 64 for fluid communication between the enclosure 34 and the drainage structure through the proximal opening 50 of the enclosure 34. As such, the medical tube 12, drainage tube 60, and enclosure 34 can form a closed passageway wherein the medical tube 12 and the drainage tube 60 are in fluid communication with each other through the enclosure 34. The medical tube assembly 10 can comprise a vacuum source 62 that can be coupled to a proximal end of the drainage tube 60 to selectively provide a vacuum that draws fluid from a patient into the medical tube 12, then from the medical tube 12 into the enclosure 34 through the distal opening 46 of the enclosure 34, and then from the enclosure 34 into the drainage tube 60 through the proximal opening 50 of the enclosure 34.

As can be seen in FIG. 6, the medical tube connector 52 can have a first internal diameter that is in continuity with an internal diameter of the medical tube 12 and a second internal diameter in continuity with an internal diameter of the distal opening 46 of the enclosure 34, thus providing the first closed passageway 54 with a continuously smooth pathway between the medical tube 12 and the distal opening 46. Similarly, as can be seen in FIG. 7, the drainage connector 56 can be a straight connector that has a variable internal diameter (similar as the medical tube connector 52 just described) that is in continuity with both an internal diameter of the drainage tube 60 and an internal diameter of the proximal opening 50 of the enclosure 34, thus providing the second closed passageway 64 with a continuously smooth pathway between the drainage tube 60 and the proximal opening 50.

Figure 8:
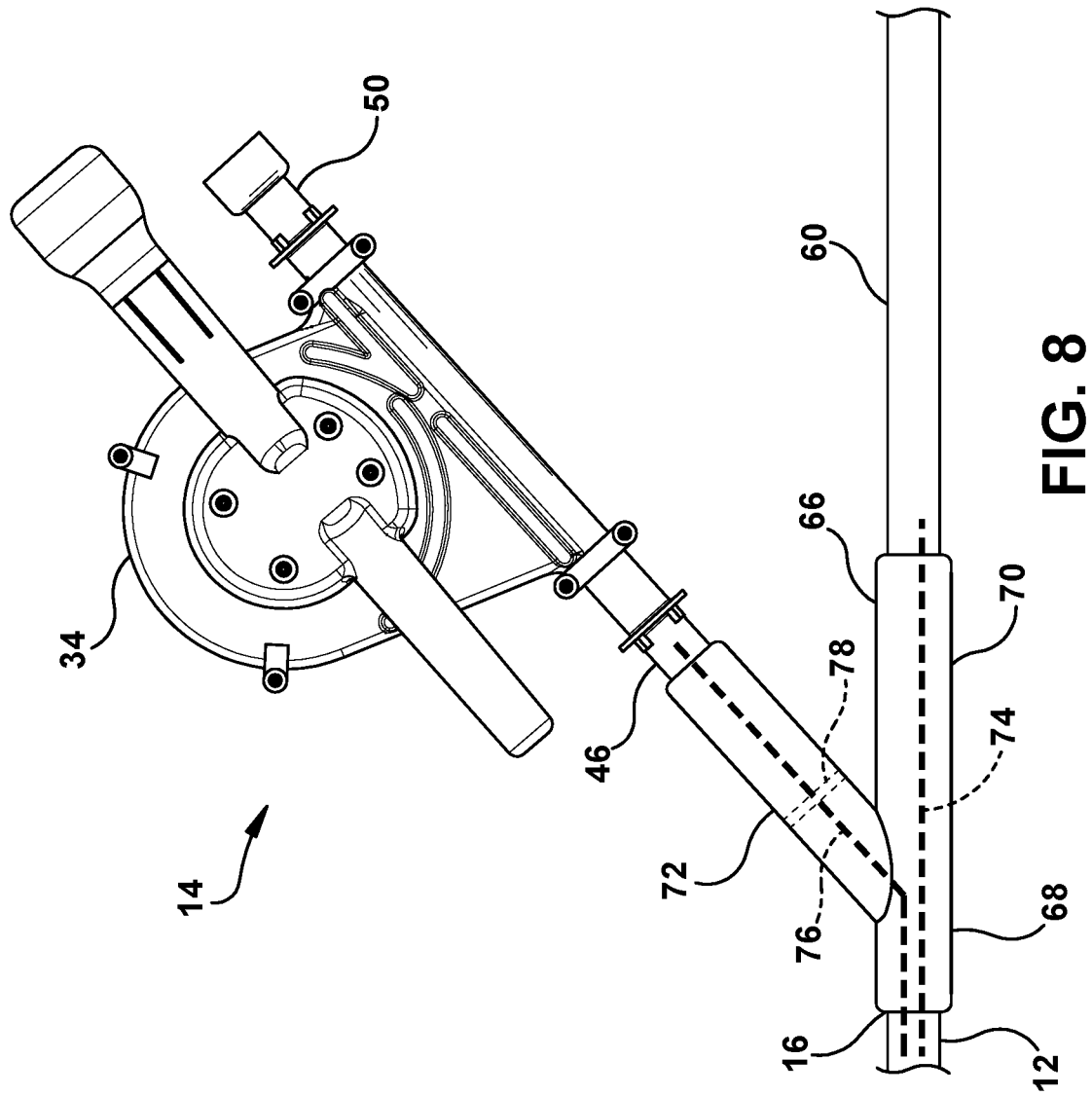
FIG. 8 is a schematic view of the device coupled to the medical tube with an example y-connector according to a first configuration.
Figure 9:
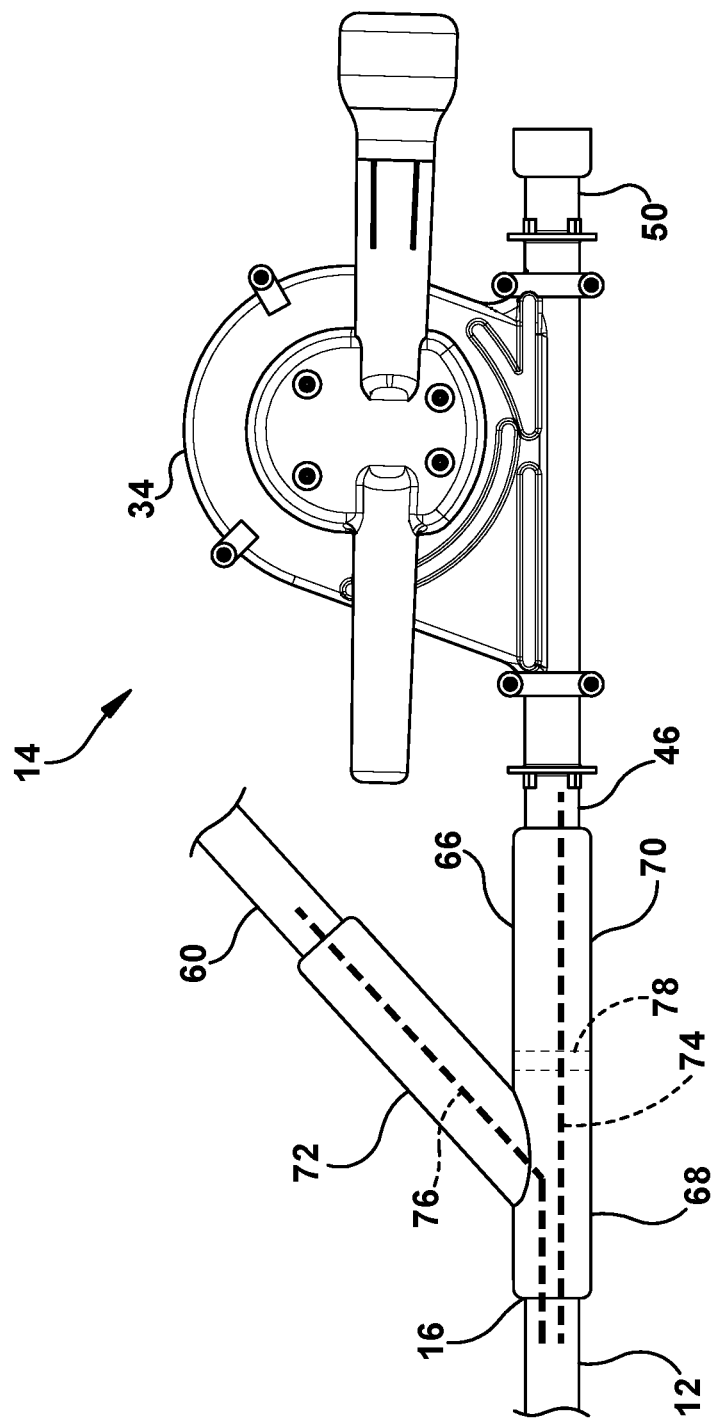
FIG. 9 is a schematic view of the device coupled to the medical tube with the example y-connector according to a second configuration.

In some embodiments, the device 14 can comprise a 3-way connecter 66 that is coupled to the distal opening 46 of the enclosure 34 and removably coupleable to the medical tube 12 and optionally the drainage tube 60, as shown in FIGS. 8 & 9. For example, the 3-way connecter 66 can comprise a primary branch 68 that splits into an axial branch 70 and a lateral branch 72. The axial branch 70 can be arranged substantially linear and coaxial with the primary branch 68 to form a linear pathway 74 and the lateral branch 72 can be arranged so that it extends in a lateral direction from the primary branch 68 to form an angled pathway 76.

The primary branch 68 of the 3-way connecter 66 can be coupled to the medical tube 12. Meanwhile, the axial and lateral branches 70, 72 can be capped or coupled to either the distal opening 46 of the enclosure 34 or drainage structure such as the drainage tube 60. For example, in one embodiment, the axial branch 70 may be coupled to the drainage tube 60 and the lateral branch 72 may be coupled with the distal opening 46 of the enclosure 34, as shown in FIG. 8. If the enclosure 34 comprises the proximal opening 50, the proximal opening 50 can be capped to close access to the enclosure 34 from the external environment through the proximal opening 50. The medical tube 12, drainage tube 60, and enclosure 34 can thus form a closed passageway wherein the medical tube 12 and the drainage tube 60 are in fluid communication with each other through the linear pathway 74. The vacuum source 62 can be coupled to the drainage tube 60 to selectively provide a vacuum that draws fluid from a patient into the medical tube 12, through the linear pathway 74, and then into the drainage tube 60 without passing through the enclosure 34.

In another embodiment, the axial branch 70 can be coupled to the distal opening 46 of the enclosure 34 and the lateral branch 72 can be coupled to the drainage tube 60, as shown in FIG. 9. If the enclosure 34 comprises the proximal opening 50, the proximal opening 50 can be capped. The medical tube 12, drainage tube 60, and enclosure 34 can thus form a closed passageway wherein the medical tube 12 and the drainage tube 60 are in fluid communication with each other through the angled pathway 76. The vacuum source 62 can be coupled to the drainage tube 60 to selectively provide a vacuum that draws fluid from a patient into the medical tube 12, through the angled pathway 76, and then into the drainage tube 60 without passing through the enclosure 34.

The connectors 52, 56, 66 described above can be rigid or flexible structures that can be coupled to the medical tube 12, enclosure 34, drainage tube 60, or other drainage structure to provide a variety of different closed passageways. Moreover, the connectors 52, 56, 66 can be coupled to the medical tube 12, enclosure 34, drainage tube 60, or other drainage structure using various means such as threaded couplings, quarter-turn locks, push-button locks, or other quick-connect means that will preserve a sterile field within and between the connected elements. Furthermore, in some embodiments, the tube 12, enclosure 34, drainage tube 60, or other drainage structure can be coupled together using other connecters such as, for example, T-connecters or connecters with more than three ports.

In some examples, the device 14 can comprise an isolation member 78 that can be configured to help isolate the enclosure 34 from the medical tube 12 when the device 14 is coupled to the medical tube 12 using a connector such as, for example, one of the connecters 52, 66 described above. For instance, when the device 14 is coupled to the medical tube 12 as shown in FIG. 8, the isolation member 78 may be provided within the lateral branch 72 of the 3-way connecter 66 to inhibit fluid communication through the lateral branch 72 but permit the guide member 22 to translate through, thus helping to isolate the enclosure 34 from the fluid and debris traveling through the linear pathway 74. As another example, when the device 14 is coupled to the medical tube 12 as shown in FIG. 9, the isolation member 78 can be provided within the axial branch 70 of the 3-way connecter 66 to inhibit fluid communication through the axial branch 70 but permit the guide member 22 to translate through, thus helping to isolate the enclosure 34 from the fluid and debris traveling through the angled pathway 76. In other examples, the isolation member 78 may be provided within the connecter 52. Indeed, in some examples, the isolation member 78 may be located in-line between the enclosure 34 and a connecter or between the medical tube 12 and a connecter. The isolation member 78 can be a seal and/or valve and may be contained within any housing.

When the device 14 is coupled to the medical tube 12 using, for example, the connecters 52, 66 described above, a closed passageway can be formed between the enclosure 34 and the medical tube 12 for the guide member 22 to extend through. More specifically, a distal portion of the guide member 22 can extend through the distal opening 46 of the enclosure 34 and into the medical tube 12. A remaining, proximal portion of the guide member 22 can remain within the enclosure 34 and coupled to the spool 20. As the guide member 22 is wound onto or off of the spool 20, the guide member 22 will be respectively retracted or advanced through the distal opening 46 of the enclosure 34 and the medical tube 12.

The device 14 can further comprise a drive mechanism 80 that is operable to rotate the spool 20 within the enclosure 34 and move the guide member 22 between an advanced state and a retracted state without compromising a sterile field within the enclosure 34; i.e. without exposing the interior of the enclosure 34 to the exterior environment. In a first example embodiment the drive mechanism 80 can comprise a drive shaft 82, a rack 88, and a pinion gear 90, as shown in FIGS. 2 & 10-11. The drive shaft 82 can extend through a drive shaft opening 92 of the enclosure 34. Moreover, the drive shaft 82 can be coaxial with and coupled to the spool 20 and in some examples the drive shaft 82 can be coaxial with and coupled to the pinion gear 90. For instance, as shown in FIG. 10, the drive shaft 82 can be an assembly comprising a stem portion 94 of the pinion gear 90 and an axle portion 96 of the spool 20 that is inserted within the stem portion 94 of the pinion gear 90 and coupled thereto. However, in some examples, the stem portion 94 of the pinion gear 90 may be inserted within the axle portion 96 of the spool 20 and coupled thereto. Moreover, in other examples, the drive shaft 82 may comprise just the stem portion 94 of the pinion gear 90 (as shown in FIG. 11), just the axle portion 96, or some other structure/assembly that extends through the drive shaft opening 92 and is coaxial with and coupled to the spool 20.

As shown in FIG. 2, the rack 88 can be provided outside of the enclosure 34 and can be engaged with the pinion gear 90 such that linear translation of the rack 88 causes the pinion gear 90 and thereby spool 20 to rotate about the axis X. In some examples, the drive mechanism 80 can comprise a handle member 98 that is coupled to the rack 88 and can be used to translate the rack 88 manually. Rotation of the pinion gear 90 causes the drive shaft 82 to rotate, which in turn causes the spool 20 to rotate. Thus, the rack 88 and pinion gear 90 of the drive mechanism 80 can be operated to rotate the spool 20 within the enclosure 34 and control translation of the guide member 22 and coupled clearance member 28 within the medical tube 12 to engage and break up clots or occluding material in the medical tube 12. As the clearance member 28 engages and breaks up clots or occluding material in the medical tube 12, suction inside of the medical tube 12 from the vacuum source 62 can draw the clots or occluding material from the medical tube 12 and through the drainage tube 60 proximally towards a drainage receptacle.

In some examples, the device 14 can further comprise a drive housing 100 for the drive mechanism 80. The rack 88 of the drive mechanism 80 can be provided within and translatable through the drive housing 100. Moreover, at least a portion of the drive shaft 82, pinion gear 90 and handle member 98 can be provided within the housing 100. For example, at least a portion of the drive shaft 82 will typically be located within the enclosure 34, such that the spool 20 is journaled for rotation about that shaft. The housing 100 can comprise one or more opening portions that provide access to an interior of the housing 100. For example, the housing 100 can comprise a drive shaft opening 102 through which the drive shaft 82 can extend, and a handle member opening portion 104 through which the handle member 98 can extend. The drive housing 100 can shield the exposed portion of the drive shaft 82 and the pinion gear 90 from debris in order to prevent contamination from encountering the seal member (hereinafter described) through which the drive shaft 82 penetrates the drive housing 100 in order to help preserve the sterility within the drive housing 100.

Figure 12:
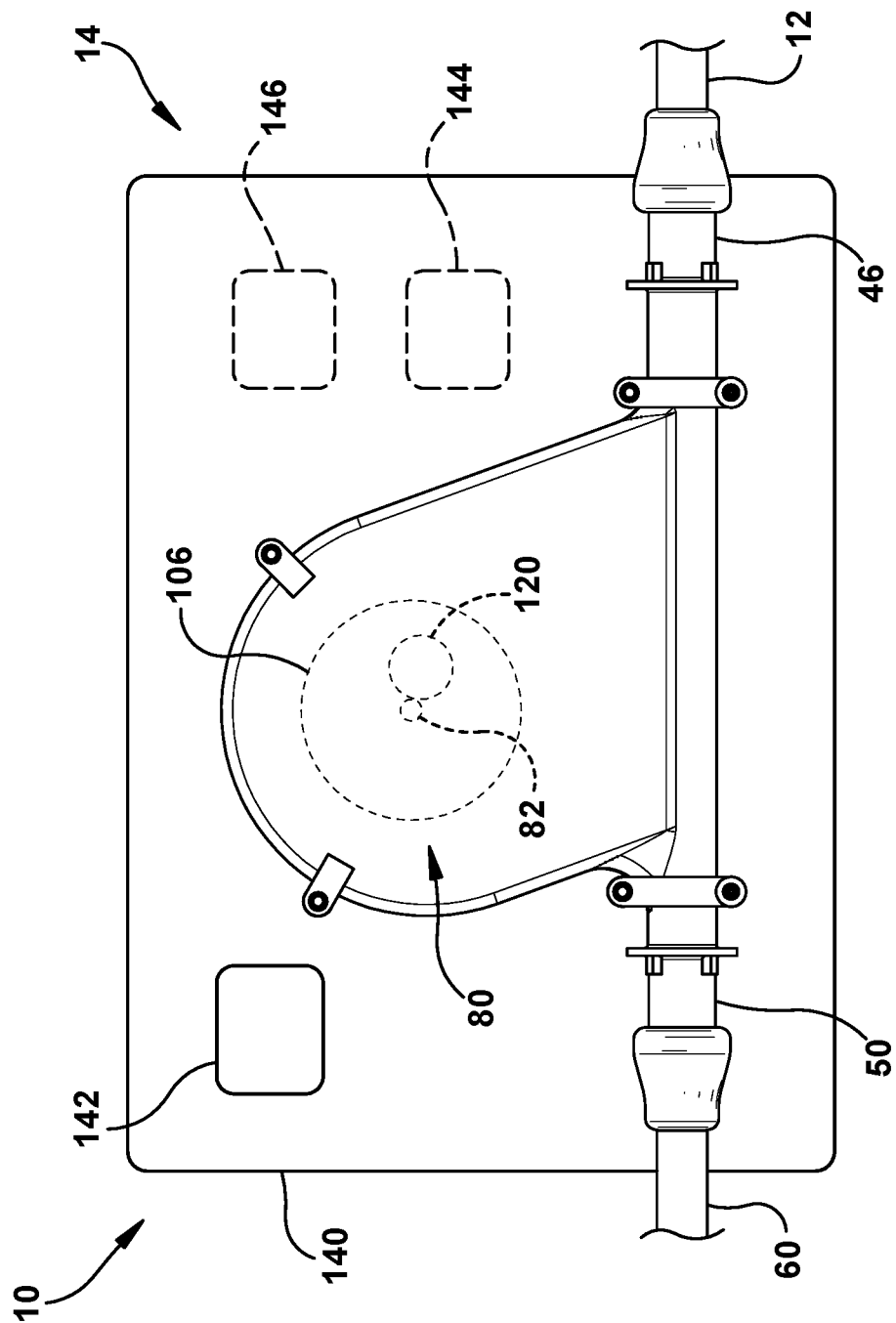
FIG. 12 is a schematic view of the device comprising a motor, a transmission mechanism, and a control system.

In a further embodiment, the drive mechanism 80 can comprise a motor 106 that is operable to selectively rotate the drive shaft 82 and the spool 20 coupled to the drive shaft 82, as shown in FIG. 12. In some examples, the motor 106 can be coupled directly to the drive shaft 82, thus replacing the pinion gear 90 and rack 88. In other examples, the motor 106 can drive the pinion gear 90, the rack 88 or some other transmission mechanism to selectively rotate the drive shaft 82 and the spool 20.

Figure 13:
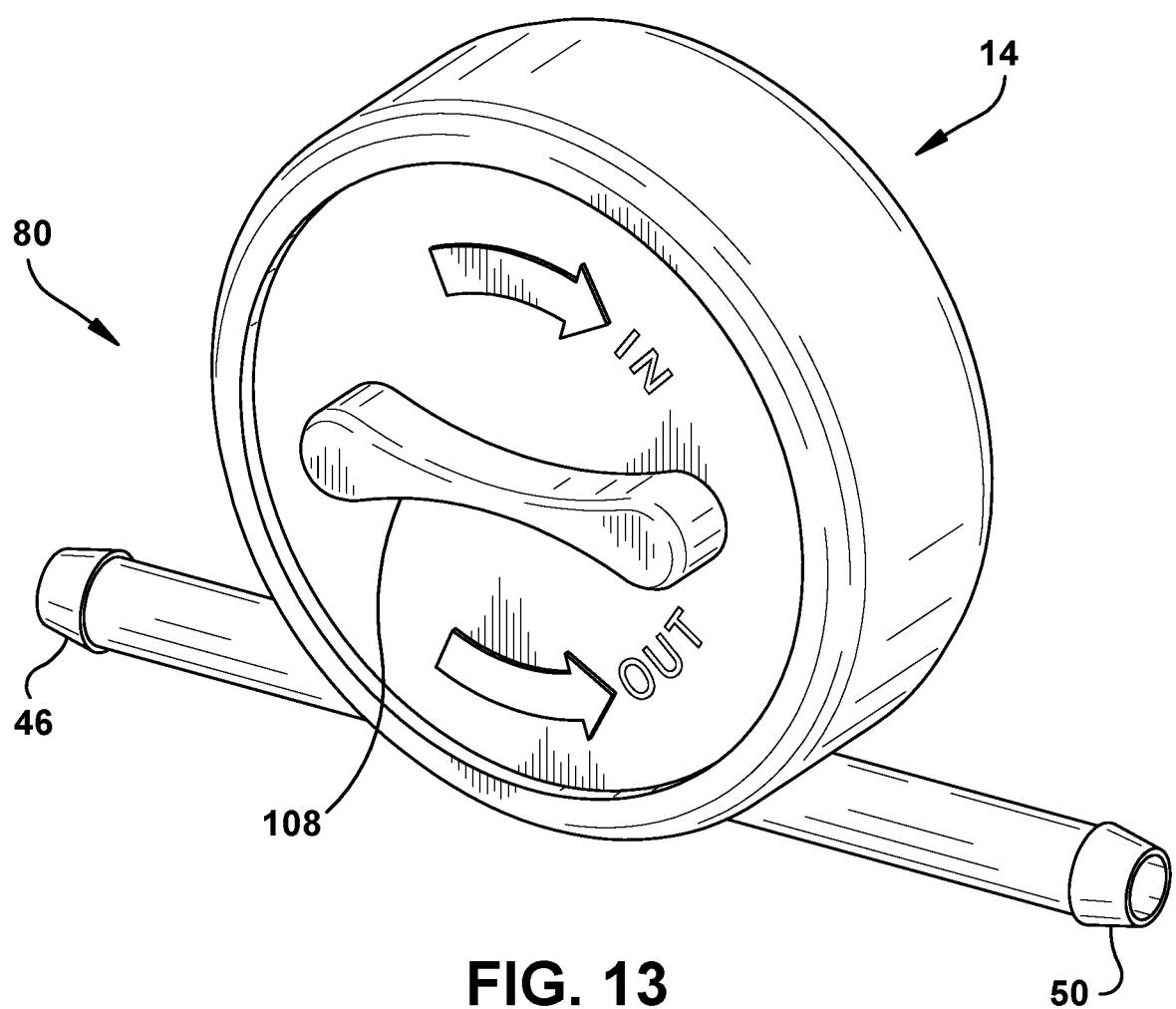
FIG. 13 is a perspective view of the device comprising a rotating knob.

In yet a further embodiment, the drive mechanism 80 can comprise a rotatable knob 108 that can be connected to rotate the drive shaft 82 and the spool 20 coupled to the drive shaft 82, as shown in FIG. 13. The knob 108 can be coupled directly to the drive shaft 82, replacing the pinion gear 90 and rack 88. In other embodiments, the knob 108 can be rotated to drive the pinion gear 90 to rotate the drive shaft 82 and the spool 20. The knob 108 can be configured such that one complete manual rotation of the knob 108 will correspond to a pre-set number of rotations of the spool 20; i.e., so that one manual rotation of the knob 108 will result in varying degrees of insertion or retraction of the guide member 22 in the medical tube 12.

In the example embodiments of the drive mechanism 80 described above, the drive shaft 82 extends through a drive shaft opening 92 of the enclosure 34 in order to couple with external elements (e.g. within drive housing 100) for rotating the shaft and thus the spool 20. Referring now to FIGS. 10-11, to help preserve the sterile field within the enclosure 34 and prevent the introduction of contaminants through drive shaft opening 92, the device 14 can further comprise a seal member 110 configured to inhibit fluid communication between the interior 36 and the exterior 38 of the enclosure 34 through the drive shaft opening 92. For instance, in some examples the seal member 110 can comprise an O-ring that is compressed between the drive shaft 82 and the drive shaft opening 92 to form a seal therebetween, as shown in FIG. 10. In other embodiments, the seal member 110 can comprise a wiper gasket (e.g., a diaphragm seal) that also forms a seal between the drive shaft 82 and the drive shaft opening 92, as shown in FIG. 11. The wiper gasket has the ability to expand and contract in the axial direction X, which can help compensate for axial movement of the drive shaft 82. Moreover, the wiper gasket can provide a seal that provides less resistance to rotation of the drive shaft 82 but still helps to preserve the sterile field within the enclosure 34.

Figure 14:
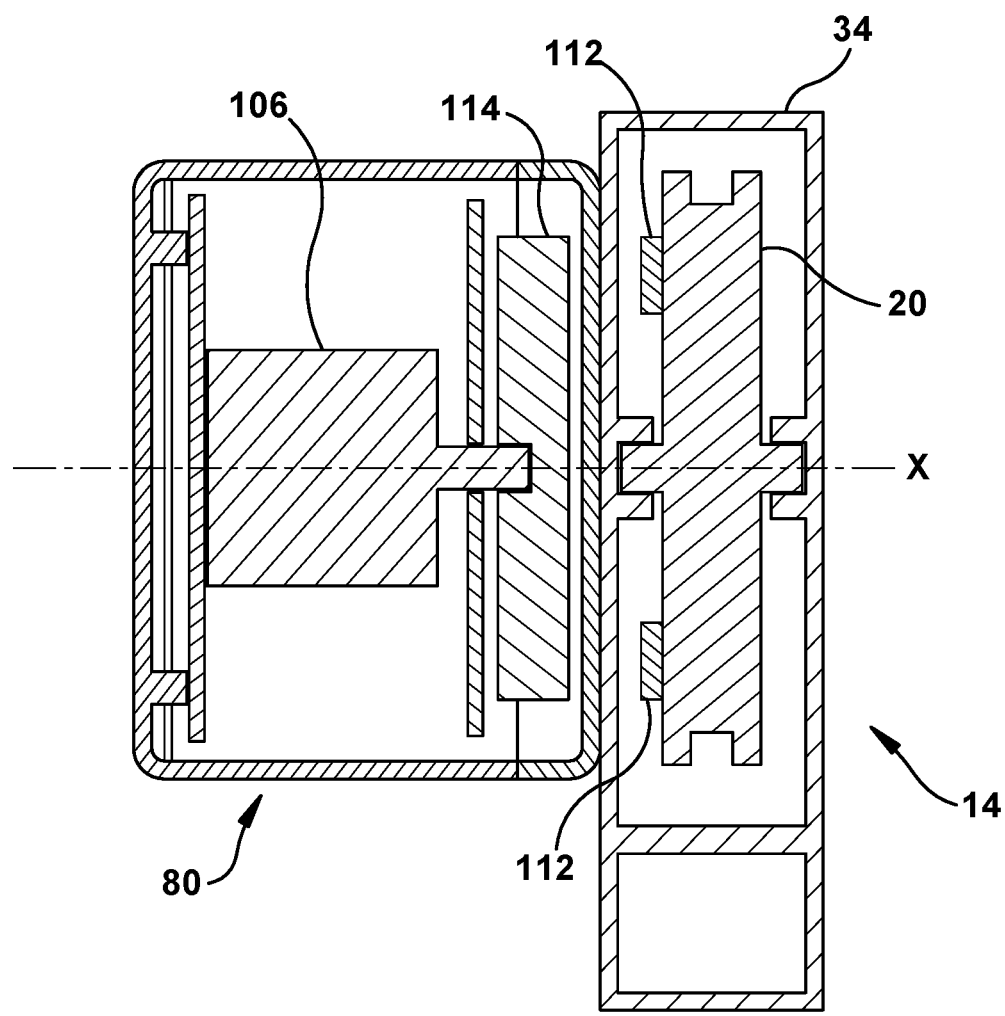
FIG. 14 is a cross-sectional of the device comprising one or more spool elements and drive elements.

Turning now to FIG. 14, in a further embodiment the drive mechanism 80 can comprise one or more magnetic spool elements 112 that are provided within the interior 36 of the enclosure 34 and coupled to the spool 20. The drive mechanism 80 can further comprise one or more magnetic drive elements 114 that are provided outside of the enclosure 34 and magnetically coupled to the one or more spool elements 112. For instance, each spool element 112 can comprise a magnet or a magnetic material that can be magnetically coupled to one or more drive elements 114 and vice versa. The magnet can comprise various shapes and sizes (e.g., round, square, bar, etc.) and can have various magnetization orientations (e.g., axial, diametric, etc.).

The drive elements 114 can be magnetically coupled to the spool elements 112 such that revolution of the drive elements 114 about the axis X causes the spool elements 112 and thereby spool 20 to rotate about that axis. To rotate the drive elements 114, the drive elements 114 can be coupled to a motor 106, which can be operable to selectively rotate the drive elements 114. In an alternative example (not shown) the drive elements 114 can be coupled to a handle or crank that can be reversibly mated to the enclosure 34 when it is desired to rotate the spool 20 within in order to actuate the clearance member. In this embodiment, the associated handle or crank can be manually rotated once the drive elements 114 have been magnetically coupled through the enclosure 34 wall to the associated spool elements 112, thereby driving the spool and actuating the clearance member.

The drive elements 114 and spool elements 112 in the embodiment described above may be provided on opposite sides of a wall of the enclosure 34 and can be magnetically coupled through the wall of the enclosure 34. Thus, in the above embodiment there is no need for a drive shaft to penetrate through an opening in the enclosure 34. As such, the magnetic actuation of the spool 20 described in the above embodiment can eliminate the need for a drive-shaft opening, thus eliminating a potential pathway for contamination of the sterile field within the enclosure 34.

In any of the example embodiments of the drive mechanism 80 described above, the drive mechanism 80 can comprise a transmission mechanism 120 that is coupled between a driving element (e.g. motor, pinion gear, rotating handle, crank, etc.) and a driven element (e.g. the drive shaft of the spool). The transmission mechanism transmits driving force from the driving element to the driven element. For example, as schematically shown in FIG. 12, the transmission mechanism 120 may be coupled to and configured to transmit rotational force between the motor 106 and the drive shaft 82. In other examples, the transmission mechanism 120 may be coupled to and configured to transmit rotational force to the drive shaft 82 from a pinion gear 90, knob 108, or any other element of the drive mechanism 80 that is movable to cause rotation of the drive shaft 82. The transmission mechanism 120 can incorporate one or a series of gears that effectively fix or adjust a drive ratio between the driving element and the driven element as known in the art. For instance, the transmission mechanism 120 can adjust or fix the drive ratio such that one complete rotation of the driving element (e.g. handle or motor crank) produces two, three, four, or any other number of corresponding rotations of the spool 20 to either wind or unwind the guide member 22. The transmission mechanism 120, if present, can be used to control the degree of rotation of the spool 20, and correspondingly how far the guide member 22 is advanced or retracted, based on the degree of rotation (e.g. manual actuation) of the driven member, such as a handle rotated by hand or a pinion gear driven by a rack 88.

Figure 15:
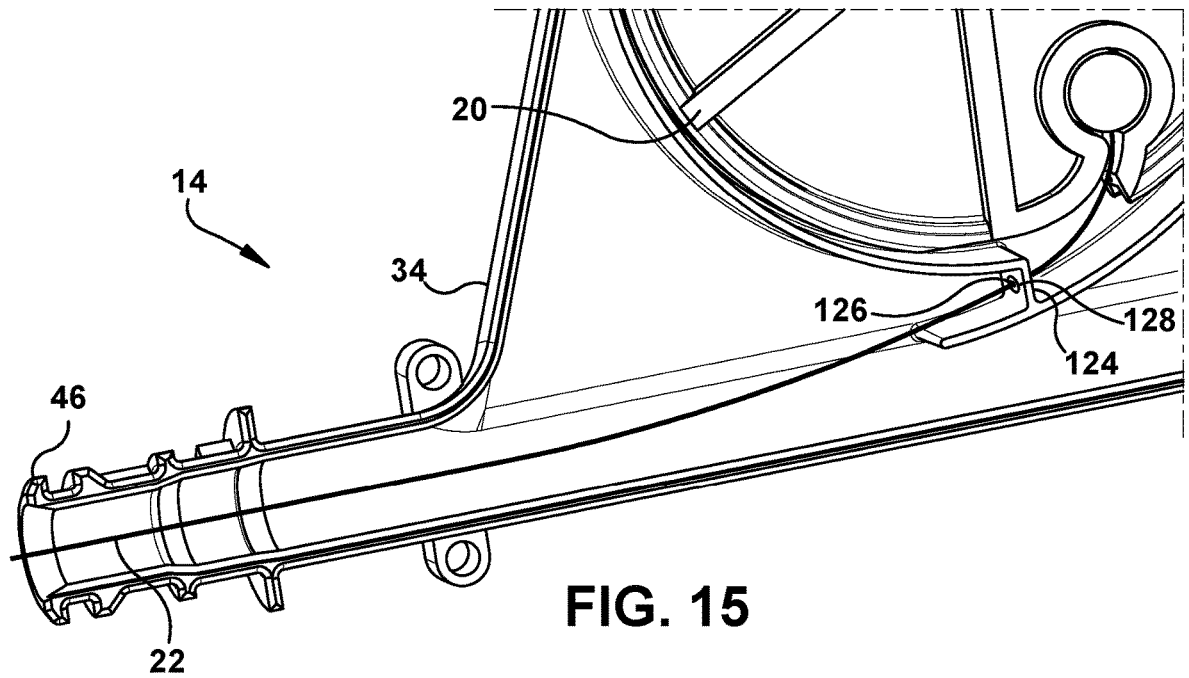
FIG. 15 is a partial broken-away view of the device showing a guide feature of the device according to one example configuration.
Figure 16:
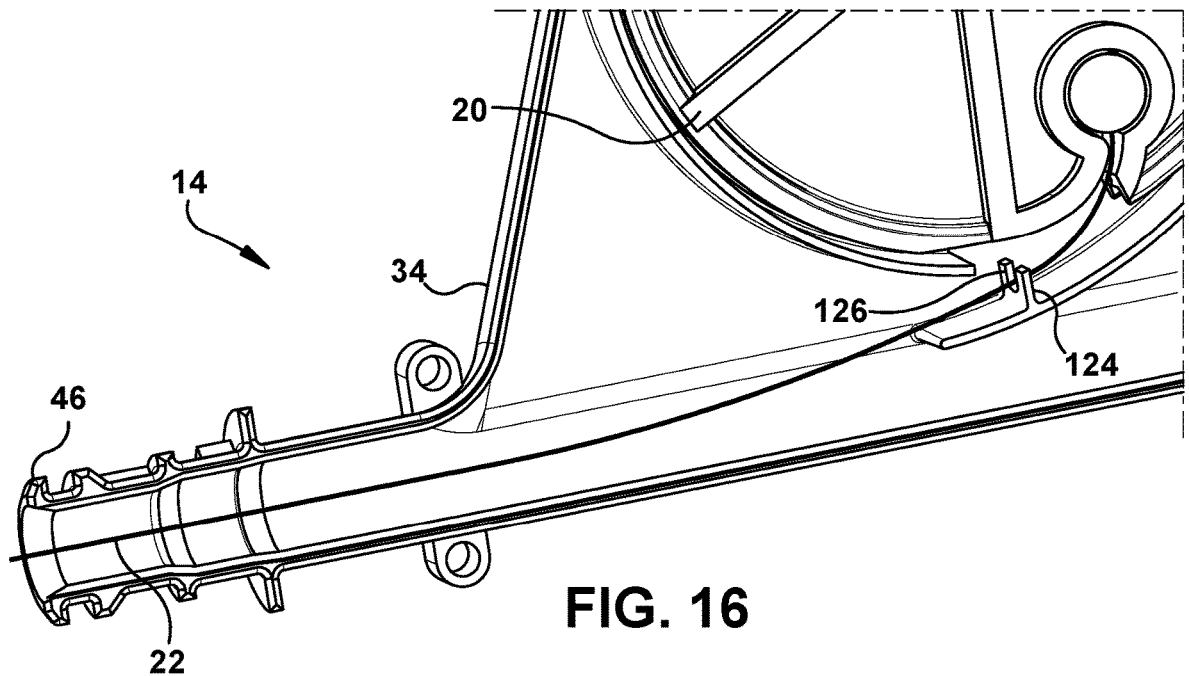
FIG. 16 is a similar view as in FIG. 15 showing the guide feature of the device according to another example configuration.

Turning now to FIGS. 15 & 16, in some embodiments the device 14 can further comprise a guide portion 124 that can be configured to help direct the guide member 22 onto or off of the spool 20. More specifically, the guide portion 124 can comprise a guide channel 126 that the guide member 22 translates through when the spool 20 is rotated. The guide channel 126 can be an aperture that extends through the guide portion 124 (as shown in FIG. 15) or the guide channel 126 can be notch or slot that extends inward from an edge of the guide portion 124 (as shown in FIG. 16). In some examples, the guide portion 124 can comprise a gasket 128 that defines the guide channel 126, as shown in FIG. 15. The gasket 128 can comprise a rubber material or any other material that can provide a smooth surface for the guide member 22 to rub against when translating through the guide channel 126. Moreover, the gasket 128 can be configured to provide a seal that inhibits the transfer of fluid or other materials through the guide channel 126 and into the area surrounding the spool 20.

The guide channel 126 can comprise a dimension that is equal to or slightly larger than a dimension of the guide member 22. For example, if the guide channel 126 is an aperture, the diameter of the aperture may be equal to or slightly larger than a diameter of the guide member 22. As another example, if the guide channel 126 is an open slot, the width of the open slot may be equal to or slightly larger than a width of the guide member 22. By "slightly larger" it is meant that the difference between the dimension of the guide channel 126 and the dimension of the guide member 22 is preferably less than or equal to 0.005 inches and still more preferably, less than or equal to 0.001 inches. When the guide channel 126 comprises a dimension that is equal to or slightly larger than a dimension of the guide member 22, the guide portion 124 can help scrape debris or other material off of the guide member 22 as the guide member 22 translates through the guide channel 126. However, the guide channel 126 can be more than slightly larger in dimension than the guide member 22 in some embodiments and in some embodiments, the guide channel 126 can be smaller in dimension than a the guide member 22 to produce an interference fit.

In some examples, the guide portion 124 can comprise a one-way elastomeric valve or brush that can be configured to scrape off the guide member 22 as the guide member 22 is wound onto or off of the spool 20. The guide portion 124 can comprise any portion that is configured to direct and/or scrape the guide member 22 as the guide member 22 is wound onto or off of the spool 20.

Figure 17:
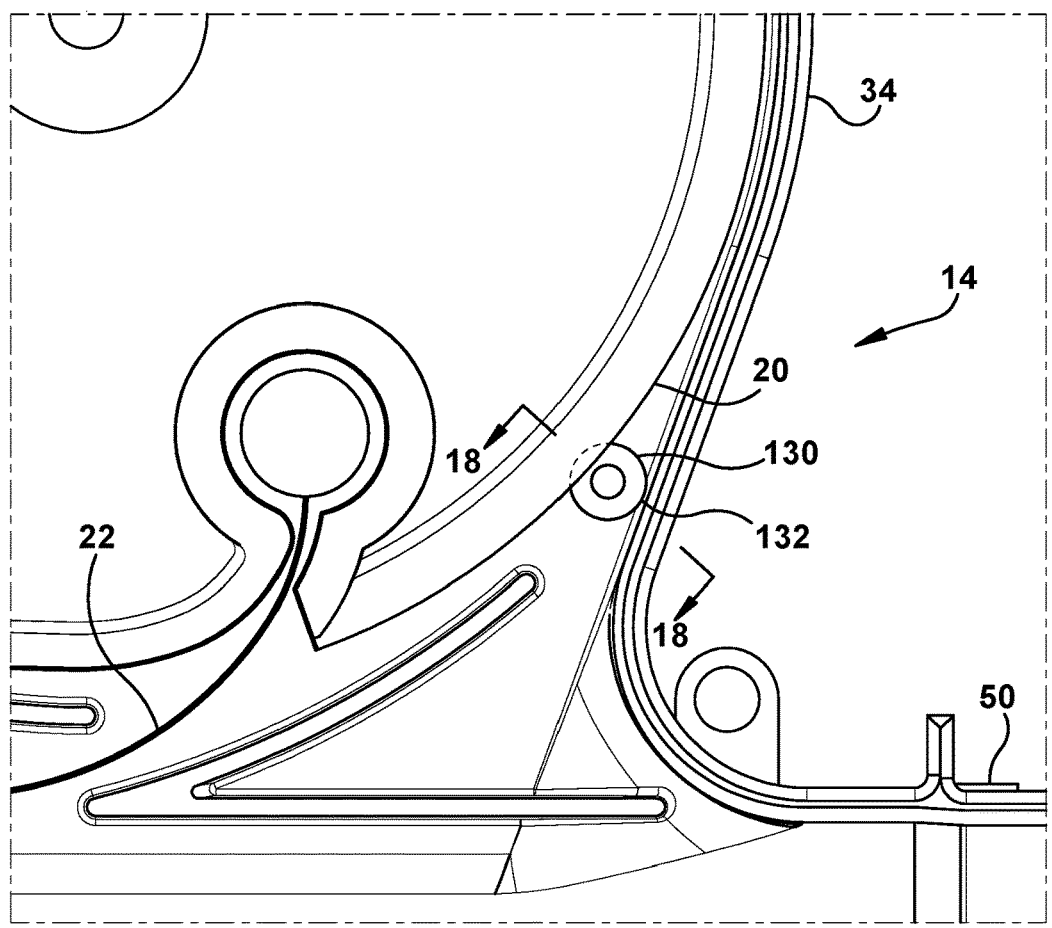
FIG. 17 is a close-up longitudinal cross-sectional view of the device showing a compression element of the device according to one example configuration.
Figure 18:
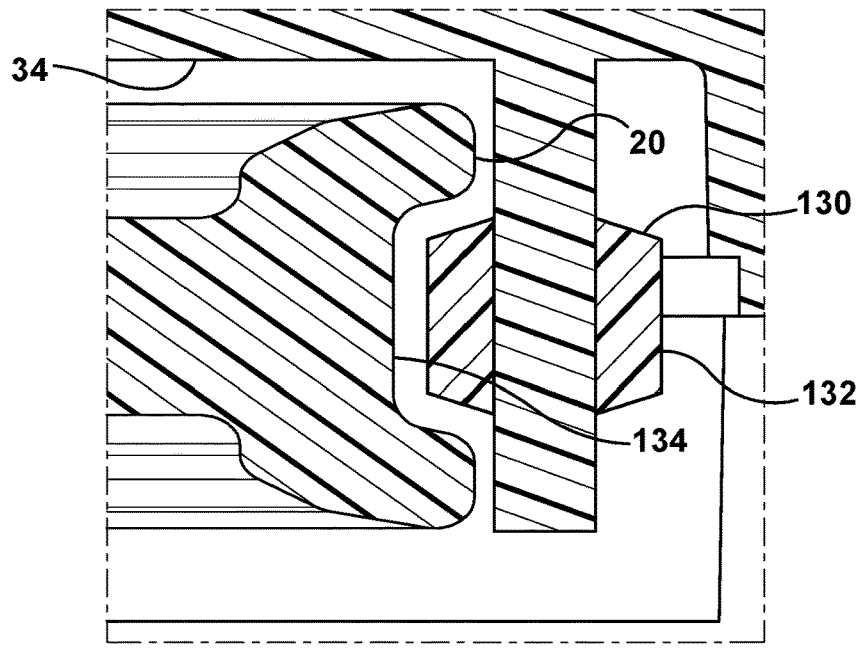
FIG. 18 is a close-up lateral cross-sectional view of the compression element shown in FIG. 17 taken along line 18-18.

In some embodiments, the device 14 can further comprise a compression element 130 that presses the guide member 22 against the spool 20 while the guide member 22 is wound about the spool 20, as shown in FIGS. 17-20. The compression element 130 can comprise one or more compression wheels 132 (as shown in FIGS. 17 & 18). The compression wheels 132 may be provided about the circumference of the spool 20 and coupled to the enclosure 34. The compression wheels 132 can be fixed within the enclosure 34 or the compression wheels 132 can be rotatable about an axis parallel to the axis X. In some examples, the spool 20 can comprise a circumferential groove 134 and the compression wheels 132 can extend at least partially within the circumferential groove 134.

Figure 19:
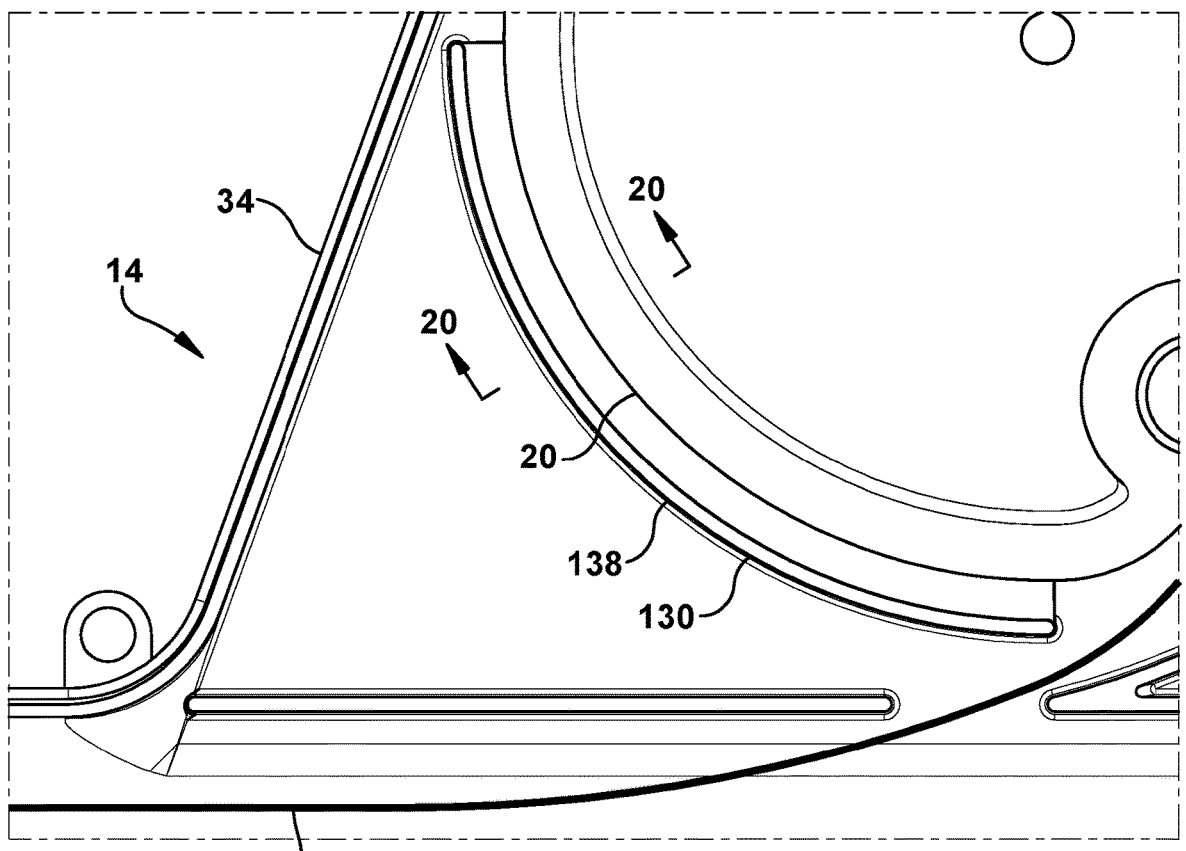
FIG. 19 is a close-up longitudinal cross-sectional view of the device showing a compression element of the device according to another example configuration.
Figure 20:
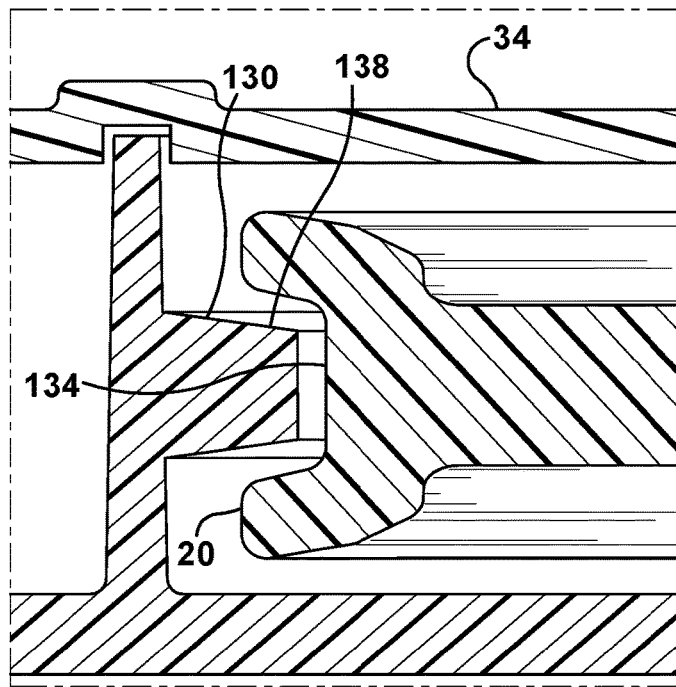
FIG. 20 is a close-up lateral cross-sectional view of the compression element shown in FIG. 19 taken along line 20-20.

The compression element 130 can additionally or alternatively comprise at least one rib 138 (as shown in FIGS. 19 & 20). The rib 138 can extend about at least a portion of the circumference of the spool 20. For examples wherein the spool 20 comprises the circumferential groove 134, the rib 138 can extend at least partially within the circumferential groove 134.

The compression wheels 132 and/or rib 138 of the compression element 130 can be distanced from the spool 20 such that a gap is provided between the spool 20 and the compression wheels 132 and/or rib 138 for the guide member 22 to extend through when wound about the spool 20. The gap can be sized such that the compression wheels 132 and/or rib 138 of the compression element 130 will press the guide member 22 against the spool 20 while the guide member 22 is wound about the spool 20, thus helping to ensure that the guide member 22 will be wound tightly against the spool 20 and inhibiting the guide member 22 from binding as the guide member 22 is wound onto or off of the spool 20.

In some embodiments, the device 14 can comprise a control system 140 configured to automatically control operation of the drive mechanism 80 and/or detect various operating parameters of the medical tube assembly 10, as shown schematically in FIG. 12.

For example, in some embodiments, the control system 140 can be configured to selectively operate the motor 106 to rotate the spool 20 and thus stroke the guide member 22 to provide one or more predetermined stroke cycles. One stroke can be an actuation of the guide member 22 from an advanced state to a retracted state and back to the advanced state. Alternatively, one stroke can be an actuation of the guide member 22 from a retracted state to an advanced state and back to the retracted state. In a further alternative, one stroke can refer to actuation of the guide member 22 only between the retracted and advanced states or vice versa. The precise scope of actuation of the guide member 22 constituting a 'stroke' in a particular case may be determined in the judgment of the clinicians responsible for patient care.

The control system 140 can be configured to stroke the guide member 22 to provide a predetermined stroke cycle wherein the guide member 22 is stroked intermittently for a set number of strokes with a set period of time between and/or during strokes. As another example, the control system 140 can be configured to stroke the guide member 22 to provide a predetermined stroke cycle wherein the guide member 22 is stroked continuously for a set number of strokes with no period of time between strokes. As another example, the control system 140 can be configured to stroke the guide member 22 to provide a predetermined stroke cycle wherein the guide member 22 is stroked only once. The control system 140 can be configured to stroke the guide member 22 to provide a plurality of different predetermined stroke cycles.

The control system 140 can comprise a user interface 142 that can permit the user to select and/or initiate execution of a predetermined stroke cycle and/or adjust variables of the stroke cycle such as how many times the guide member 22 should be stroked, how much time is between strokes, a position of the guide member 22 in the retracted state, a position of the guide member 22 in the advanced state, or any other variable. The user interface 142 can comprise a touch-screen, one or more switches or buttons, or any other feature that permits a user to select and/or initiate execution of the predetermined stroke cycle and/or adjust variables of the stroke cycle.

In some embodiments, the control system 140 can comprise a sensor 144 configured to detect one or more operating parameters of the medical tube assembly 10. For example, in one embodiment the sensor 144 can be configured to detect at least one or more of the following operating parameters: a) a degree of translation of the guide member 22 and/or clearance member 28; b) a degree of rotation of the spool 20; c) a length and/or position of the distal opening 18 of the medical tube 12; d) a torque in the drive mechanism 80 such as, for example, a torque in the drive shaft 82, pinion gear 90, or the axle portion 96 of the spool 20; e) a pressure in the medical tube 12; f) a pressure in the drainage tube 60; and g) any other operating parameter of the medical tube assembly 10. For instance, the sensor 144 may be a continuity circuit used to detect a position of a break/or cut in the medical tube 12, a hall effect sensor, a torque sensor, a pressure sensor, or some other type of sensor configured to detect one or more operating parameters of the medical tube assembly 10.

The control system 140 can be configured to selectively operate the motor 106 based on the operating parameter detected by the sensor 144. For instance, if the sensor 144 detects a pressure in the medical tube 12 or drainage tube 60 that indicates the presence of an obstruction in the medical tube 12, the control system 140 can be configured to operate the motor 106 to stroke the guide member 22 and coupled clearance member 28 through the medical tube 12 and help dislodge and/or draw the obstructing material within the medical tube 12. As another example, if the sensor 144 detects a torque in the drive mechanism 80 during operation that exceeds an upper limit set for the motor 106 or some other component of the drive mechanism 80, the control system 140 can be configured to stop operation of the motor 106 and optionally sound an alarm.

In some embodiments, the operating parameter detected by the sensor 144 may be defined to have a lower limit and/or upper limit for each variable. Moreover, the control system 140 can comprise an alarm 146 that is configured to selectively activate based on the operating parameter detected by the sensor 144. For example, the alarm 146 can be configured to activate when the detected operating parameter is at or below the lower limit or at or above the upper limit. For instance, the alarm 146 can be configured to activate when a detected torque in the drive mechanism 80 exceeds an upper limit for the motor 106 or some other component of the drive mechanism 80.

Figure 21:
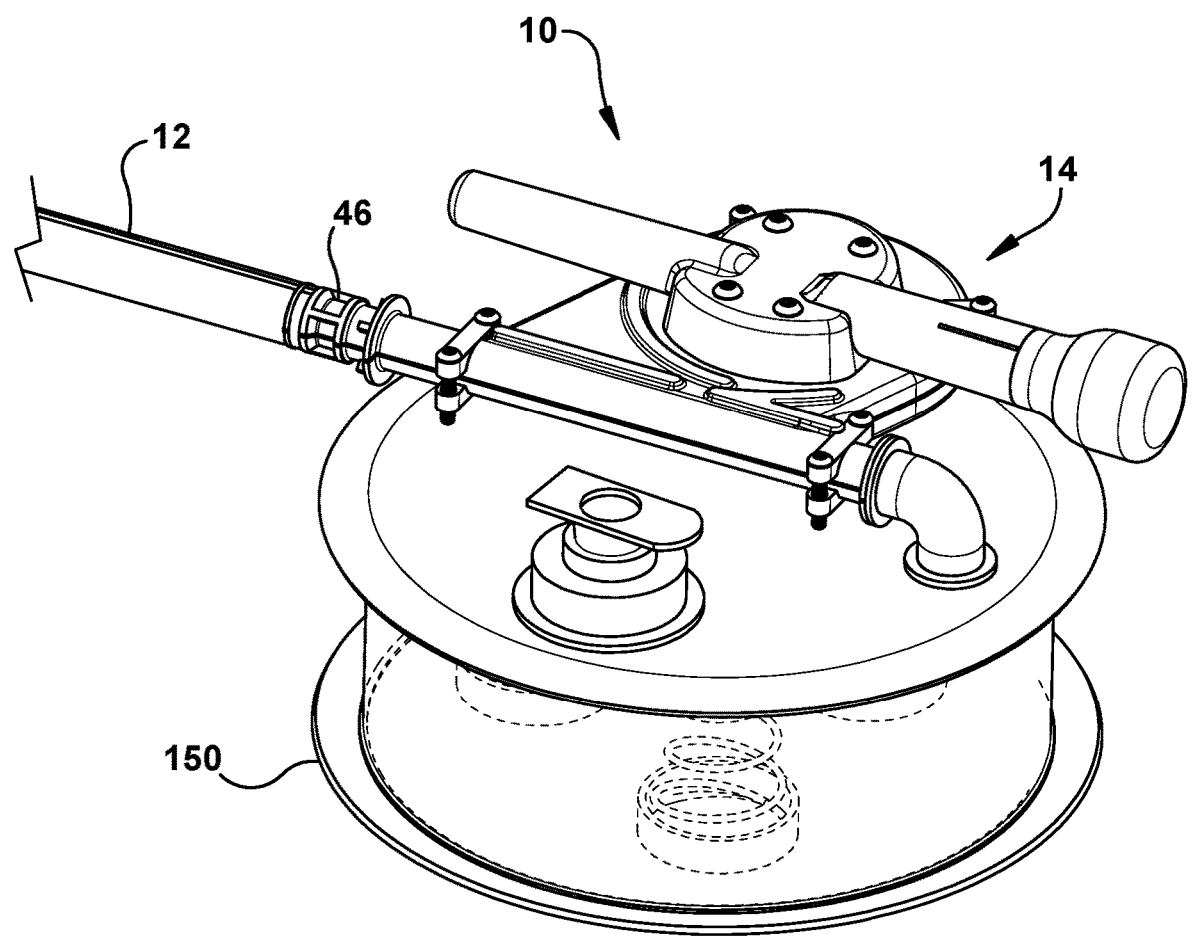
FIG. 21 is a perspective view of one embodiment of the medical tube assembly that comprises a drainage receptacle.

The medical tube assembly 10 can comprise a drainage receptacle 150 into which material passing through the device 14 and/or drainage tube 60 can be delivered, as shown in FIG. 21. FIG. 21 shows an onboard drainage receptacle that is portable and coupled to the clearance device 14, however other configurations are possible. In the illustrated embodiment the device 14 is coupled to the receptacle 150 and oriented such that the medical tube connected thereto extends at an angle (e.g. a 90° angle) relative to the pathway through a port in the receptacle 150 through which evacuated obstructing material will be deposited into the receptacle 150. In this embodiment such material will negotiate a bend or turn in the vacuum pathway (as shown in FIG. 21). Alternatively, the device 14 can be oriented such that its connection to the medical tube 12 results in a substantially linear path from the medical tube 12 into the receptacle 150 through the aforementioned port so that evacuated obstructing material will be deposited into the canister 150 along a substantially linear vacuum pathway and the elbow shown in FIG. 21 (or other path-redirecting structure) will not be necessary.

The receptacle 150 can take on a variety of different configurations without departing from the scope of the invention. For example, the receptacle 150 can be a spring loaded drainage canister, a bulb drain canister, a chest drainage canister, or any other type of drainage receptacle into which material passing through the device 14 and/or drainage tube 60 can be delivered.

As described above, the device 14 of the medical tube assembly 10 can be coupled to the medical tube 12 and the drive mechanism 80 of the device 14 can be operated to rotate the spool 20 and actuate the guide member 22 and coupled clearance member 28 through the medical tube 12 to help dislodge and/or draw the obstructing material within the medical tube 12. In some embodiments, the device 14 can comprise additional means to assist in actuation of the guide member 22 such as, for example, ultrasonic vibration or a magnetic shuttle coupled to the medical tube 12. Moreover, in some embodiments, one or more features of the medical tube assembly 10 can be configured to help control how far the clearance member 28 translates through the medical tube 12 during actuation of the guide member 22.

For example, in some embodiments, the device 14 can be operable to move the clearance member 28 between a retracted state and a fully advanced state and one or more features of the device 14 can be calibrated to the medical tube 12 such that when the device 14 is coupled with the medical tube 12 and the clearance member 28 is in the fully advanced state, the clearance member 28 will be located at a predetermined location L1 within the medical tube 12 (see FIG. 1). As discussed in further detail below, the predetermined location L1 can be a location relative to an end of the medical tube 12 or some other portion of the medical tube 12.

For instance, in one example, the spool 20 of the device 14 can be manually or automatically rotated from a first position wherein the guide member 22 is at least partially wound about the spool 20 and the clearance member 28 is in a retracted state to a second position, wherein the guide member 22 is fully unwound from the spool 20 and the clearance member 28 is in the fully advanced state. The length of the guide member 22 can be calibrated such that when the device 14 is coupled with the medical tube 12 and the clearance member 28 is in the fully advanced state, the clearance member 28 will be located at the predetermined location L1 within the medical tube 12.

In another example, the control system 140 can be configured to selectively operate the motor 106 to rotate the spool 20 and stroke the guide member 22 such that the clearance member 28 moves between a fully advanced state and a retracted state, wherein when the device 14 is coupled with the medical tube 12 and the clearance member 28 is in the fully advanced state, the clearance member 28 will be located at the predetermined location L1 within the medical tube 12. For instance, in some examples the sensor 144 of the control system 140 can be configured to detect a length and/or position of the distal opening 18 of the medical tube 12 by using, for example, a hall effect sensor, a continuity circuit used to detect a position of a break and/or cut in the medical tube 12, or some other means. Based on the detected measurement, the control system 140 can provide a predetermined stroke cycle for the guide member 22 to stroke the guide member 22 such that when the clearance member 28 is in a fully advanced state, the clearance member 28 will be located at the predetermined location L1 within the medical tube 12. In other examples, the user interface 142 of the control system 140 can be used to select or set a predetermined stroke cycle for the guide member 22 to stroke the guide member 22 such that the clearance member 28 moves between a fully advanced state and a retracted state, wherein when the clearance member 28 is in the fully advanced state, the clearance member 28 will be located at the predetermined location L1 within the medical tube 12. The control system 140 can be configured in a variety of ways to stroke the guide member 22 such that the clearance member 28 moves between a fully advanced state and a retracted state, wherein when the clearance member 28 is in the fully advanced state, the clearance member 28 will be located at the predetermined location L1 within the medical tube 12.

The predetermined location L1 can be a location relative to the distal opening 18 of the medical tube 12 that is located within the medical tube 12 such that the clearance member 28 is preferably within 2 cm of the distal opening 18 and more preferably, within 1 cm of the distal opening 18 at the predetermined location L1. This can help ensure that the clearance member 28 passes through a substantial portion of the medical tube 12 when moving between its fully advanced state to its retracted state to help dislodge and/or draw the obstructing material within the medical tube 12. Still more preferably, the predetermined location L1 can be located within the medical tube 12 such that the clearance member 28 is spaced a distance from the distal opening 18 that is equal to or greater than 0.5 cm. This can help ensure that the clearance member 28 will not extend through the distal opening 18 of the medical tube 12 during actuation of the clearance member 28. However, in other embodiments, the predetermined location L1 can be a location relative to the proximal opening 16 that is located such that the clearance member 28 is a certain predetermined distance from the proximal opening 16 of the medical tube 12. Moreover, in some embodiments, the predetermined location L1 can be a location relative to other structure of the medical tube 12 such as, for example an aperture of the medical tube 12. The predetermined location L1 can be located such that the clearance member 28 is distal or proximal of an aperture in the medical tube 12 in the fully advanced position. The predetermined location L1 can be a location located anywhere and relative to any structure within the medical tube 12 without departing from the scope of the invention.

Figure 22:
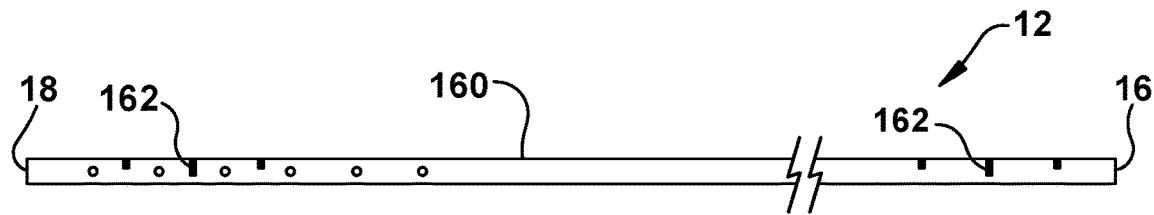
FIG. 22 is a schematic view of the medical tube according to one example embodiment.
Figure 23:
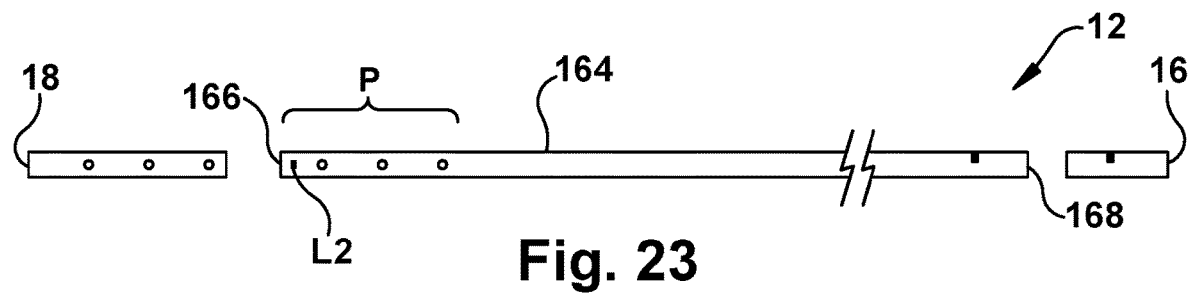
FIG. 23 is a schematic view of the medical tube shown in FIG. 22 after being cut.

In other embodiments, the length of the medical tube 12 can be calibrated to the device 14 and a patient. More specifically, the length of the medical tube 12 can be adjusted such that when the device 14 is coupled with the length adjusted medical tube and the clearance member 28 is in the fully advanced state, the clearance member 28 will be located at a predetermined or user-selected location within the adjusted medical tube. Moreover, the length of the medical tube 12 can be adjusted such that a distal, residing portion P of the adjusted medical tube will be correctly sized for a patient. For instance, in one example the medical tube 12 can comprise a main body 160 and at least one pair of markings 162 that is arranged on the main body 160 such that cutting the main body 160 at each marking 162 will create a cut tube portion 164 with a distal end 166 and a proximal end 168, as shown in FIGS. 22 & 23. Each marking 162 can be a drawn line, a notch, a projection, or any other feature that can indicate a position to cut the main body 160. Moreover, a plurality of such markings 162 can be provided as graduations along a line or multiple lines that are aligned with a longitudinal axis of the medical tube 12 in order to facilitate a desired residing-portion P length (which will reside inside a patient in use) while ensuring that the overall length of the medical tube 12 is calibrated to accommodate the clearance member 28 in its fully-advanced state.

By cutting the main body 160 at a selected marking 162 near its distal end, the cut tube portion 164 will have a distal, residing portion P (e.g. wherein apertures for the drainage of fluid are provided in the tube 12) having a predetermined or user-selected length. The residing portion P can be a portion of the cut tube portion 164 that is intended to reside entirely within a patient when the distal end 166 of the cut tube portion 164 is located in a desired compartment of a patient. For instance, the residing portion P can be defined by a section of the cut tube portion P having a branched lumen or a plurality of apertures (noted above) that is desired to reside entirely within the patient. By cutting the main body 160 at a selected marking 162 near its distal end, the residing portion P can have a predetermined or user-selected length matched to a patient such that when the distal end 166 of the cut tube portion 164 is located in a desired compartment of the patient, the residing portion P will reside entirely within the patient and will not extend outside of the patient.

By cutting the main body 160 at the marking 162 near its proximal end that corresponds to the marking 162 where the tube was cut near its distal end (to define the length of the residing portion P), the cut tube portion 164 will be configured such that when the device 14 is coupled with the cut tube portion 164 and the clearance member 28 is in the fully advanced state, the clearance member 28 will be located at a predetermined or user-selected location L2 within the cut tube portion 164. The location L2 can be a location relative to the distal end 166 that is located within the cut tube portion 164 such that the clearance member 28 is preferably within 2 cm of the distal end 166 and more preferably, within 1 cm of the distal end 166 at the location L2. Still more preferably, the location L2 can be a location within the cut tube portion 164 such that the clearance member 28 is spaced a distance from the distal end 166 that is equal to or greater than 0.5 cm. However, the location L2 can be any predetermined or user-selected location relative to any structure of the cut tube portion 164 without departing from the scope of the invention.

In the example described above, the at least one pair of markings 162 is configured for calibration of the medical tube 12 for use with the device 14 described above and to produce a residing portion P having a particular, predetermined or user-selected length. However, in some embodiments, the at least one pair of markings 162 can similarly be configured for calibration of the medical tube 12 for use with other devices that are operable to move a clearance member between a fully advanced state and a retracted state. Furthermore, the length of the produced residing portion P can vary in different embodiments. Still further, in some embodiments the medical tube 12 can comprise multiple pairs of associated markings, wherein each pair of associated markings is configured to produce an residing portion P having a particular length and to calibrate the medical tube 12 for use with a particular device that is operable to move a clearance member between a fully advanced state and a retracted state. In this manner, the medical tube 12 can be calibrated using the pairs of markings for use with various clearance devices and to produce residing portions P of various lengths that are matched to a particular patient/procedure. If multiple pairs of markings are provided, each pair can be distinguished using different numbers, letters, colors, marking lengths, or any other means to distinguish between the multiple pairs of markings.

Figure 24:
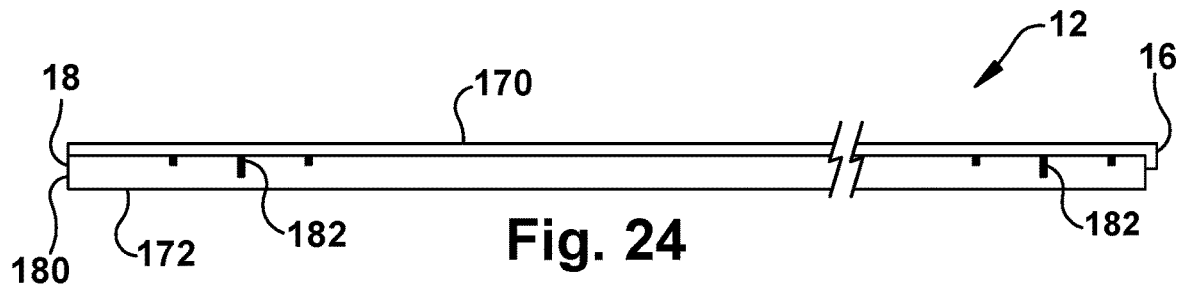
FIG. 24 is a schematic view of the medical tube according to another example embodiment.
Figure 25:
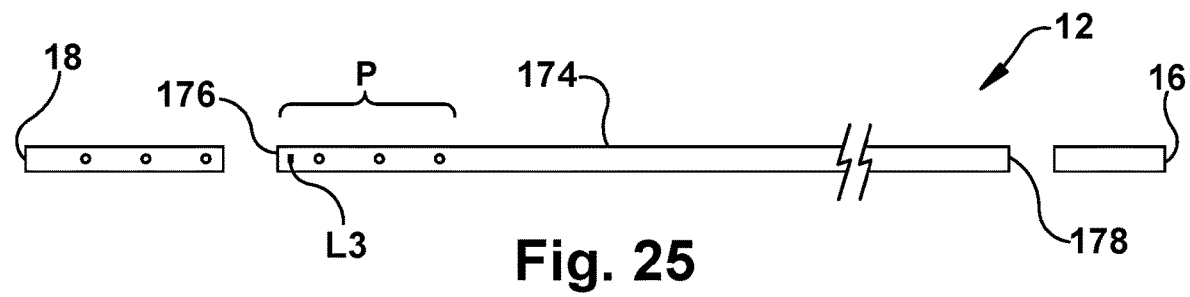
FIG. 25 is a schematic view of the medical tube shown in FIG. 24 after being cut.

In another example, the medical tube 12 can comprise a main body 170 and the medical tube assembly 10 can comprise an indicator device 172 that is configured to be aligned with the medical tube 12 such that alignment with the medical tube 12 will indicate a pair or respective pairs of locations to cut the main body 170 at to create a cut tube portion 174 having a calibrated length with a distal end 176 and a proximal end 178, as shown in FIGS. 24 & 25. For instance, in one example, the indicator device 172 can be a guide that comprises an end 180 and at least one pair of indicators 182. The indicator device 172 can be aligned longitudinally with the medical tube 12 such that the end 180 is aligned with the proximal opening 16 or distal opening 18 of the medical tube 12. When aligned as such, the pair of indicators 182 can indicate a pair of locations to cut the main body 170 to create the cut tube portion 174. Each indicator 182 can be a line, a notch, a projection, an aperture, or any other feature that can indicate a location along its length. In other examples, the indicator device 172 can be a sleeve that the medical tube 12 can be inserted into, wherein when the medical tube 12 is inserted within, a pair of indicators of the sleeve can indicate a pair of locations to cut the main body 170 to create the cut tube portion 174. The indicator device 172 can be any device configured to be aligned with the medical tube 12 such that alignment with the medical tube 12 will indicate a pair or pairs of locations to cut the main body 170 to create a cut tube portion 174 having a calibrated length while defining a desired-length residing portion P.

By cutting the main body 170 at an indicated location near its distal end, the cut tube portion 174 will have a distal, residing portion P having a predetermined or user-selected length as described above. The residing portion P can be a portion of the cut tube portion 174 that is intended to reside entirely within a patient as described above. For instance, the residing portion P can be defined by a section of the cut tube portion P having a branched lumen or a plurality of apertures that is desired to reside entirely within the patient. By cutting the main body 170 at a particular indicated location near its distal end, the residing portion P can have a predetermined or user-selected length matched to a patient such that when the distal end 176 of the cut tube portion 174 is located in a desired compartment of the patient, the residing portion P will reside entirely within the patient and will not extend outside of the patient.

By cutting the main body 170 at the indicated location near its proximal end that is associated with or corresponds to the indicated location where it was cut near its distal end, the cut tube portion 174 will be configured such that when the device 14 is coupled with the cut tube portion 174 and the clearance member 28 is in the fully advanced state, the clearance member 28 will be located at a predetermined or user-selected location L3 within the cut tube portion 174. The location L3 can be a location relative to the distal end 176 that is located within the cut tube portion 174 such that the clearance member 28 is preferably within 2 cm of the distal end 176 and more preferably, within 1 cm of the distal end 176 at the location L3. Still more preferably, the location L3 can be a location within the cut tube portion 174 such that the clearance member 28 is spaced a distance from the distal end 176 that is equal to or greater than 0.5 cm. However, the location L3 can be any location relative to any structure of the cut tube portion 164 without departing from the scope of the invention.

In the example described above, the at least one pair of indicators 182 is configured for calibration of the medical tube 12 for use with the device 14 described above and to produce a residing portion P having a particular, predetermined or user-selected length. However, in some embodiments the at least one pair of indicators 182 can be similarly configured for calibration of the medical tube 12 for use with other devices that are operable to move a clearance member between a fully advanced state and a retracted state. Furthermore, the predetermined or user-selected length of the residing portion P can vary in different embodiments. Still further, in some embodiments the indicator device 172 can comprise multiple pairs of indicators, wherein each pair of indicators is configured to produce a residing portion P having a particular, predetermined or user-selected length and to calibrate the medical tube 12 for use with a particular device that is operable to move a clearance member between a fully advanced state and a retracted state. In this manner, the medical tube 12 can be calibrated using the indicator device 172 to be used with various clearance devices and to produce residing portions P of various lengths matched to a particular patient/procedure. If multiple pairs of indicators are provided, each pair can be distinguished using different numbers, letters, colors, indicator portion lengths, or any other means to distinguish between the multiple pairs of indicator portions.

An example method 200 will now be described of calibrating a medical tube for a clearance device that is operable to move a clearance member of the clearance device between a fully advanced state and a retracted state. The clearance device may be the device 14 described above or the clearance device may be some other clearance device. As shown in FIG. 26, the method 200 can comprise the step 202 of providing a medical tube comprising a main body such as, for example, the medical tube 12 comprising the main body 160 described above. The method 200 can further comprise the step 204 of cutting the main body to create a cut tube portion with a distal end and a proximal end, the cut tube portion being configured such that when the cut tube portion is coupled with the clearance device and the clearance member is within the cut tube portion in the fully advanced state, the clearance member will be located at a predetermined location within the cut tube portion. The produced cut tube portion can also have a distal, residing portion comprising a predetermined length such that when a distal end of the cut tube portion is located in a desired compartment of a patient, the residing portion will be located entirely within the patient such that the residing portion P will not extend outside of the patient. For example, the medical tube 12 can comprise the at least one pair of markings 162 described above and the step 204 can comprise the step of cutting the main body 160 at the markings 162 to create the cut tube portion. As another example, the step 204 can comprise the steps of a) providing an indicator device comprising an indicator portion such as, for example, the indicator device 172 comprising the at least one pair of indicator portions 182 described above; b) aligning the indicator device with the medical tube such as, for example, by aligning the end 180 of the indicator device 172 the proximal opening 16 or distal opening 18 of the medical tube 12; and c) cutting the main body at a location indicated by the pair of indicator portions to create the cut tube portion.

As shown in FIG. 27, in a further method 210 a step 212 of coupling the medical tube 12 to the distal opening 42 of the device 14 is performed, for example by using either of connectors 52, 66 as described above. The method 210 can further comprise the step 214 of operating the drive mechanism 80 to rotate the spool 20 and thereby move the guide member 20 and coupled clearance member 28 within the medical tube 12 between an advanced state and a retracted state without compromising a sterile field within the enclosure 34. For example, the drive mechanism 80 can be operated using the rack 88 and pinion gear 90, the motor 106, the knob 108, the one or more drive elements 114, and/or the control system 140 as discussed above. The method 210 can further comprise the step 216 of applying a vacuum to the medical tube 12 while the guide member 20 and coupled clearance member 28 are moved between the advanced state and retracted state. This can be accomplished for example by coupling one end of the drainage tube 60 to the vacuum source 62 and another end of the drainage tube 60 to either the proximal opening 50 of the device 14 or the 3-way connecter 66 and then operating the vacuum source 62 to apply the vacuum.

Illustrative embodiments have been described, hereinabove. It will be apparent to those skilled in the art that various modifications and variations can be made without departing from the spirit and scope of the claimed invention. It is intended to include all such modifications and alterations within the scope of the present invention.

What is claimed is:

1. A medical device for clearing obstructions from a medical tube, the medical device comprising:
    an enclosure defining (i) an interior comprising a sterile field and having a discrete spool chamber isolated from a remainder of the interior, (ii) an exterior, and (iii) an opening for providing access to the interior;
    a drive mechanism;
    a rotatable spool located within the discrete spool chamber;
    a control system configured to automatically control operation of the drive mechanism; and
    an elongated guide member at least partially wound on the rotatable spool;
    the drive mechanism being configured to (i) advance the elongated guide member out of the enclosure through the opening without compromising the sterile field and (ii) withdraw the elongated guide member into the enclosure through the opening without compromising the sterile field,
    the interior further comprising a discrete conduit in communication with and extending substantially tangentially of said spool chamber.

2. The medical device of claim 1, wherein the elongated guide member is coupled to the spool such that rotation of the spool accommodates the elongated guide member to wind or unwind about the spool as the elongated guide member is withdrawn or advanced, respectively, into or out from said enclosure through said opening.

3. The medical device of claim 2, wherein the drive mechanism further comprises a drive shaft extending through a drive shaft opening of the enclosure and being coaxial with the spool, wherein rotation of the drive shaft is configured to cause the rotation of the spool.

4. The medical device of claim 3, further comprising a seal member configured to inhibit fluid communication between the interior of the enclosure and the exterior of the enclosure through the drive shaft opening.

5. The medical device of claim 4, wherein the seal member comprises an O-ring or a wiper gasket and provides a seal between the drive shaft and the drive shaft opening.

6. The medical device of claim 3, wherein the drive mechanism further comprises a motor configured to selectively rotate the drive shaft and the spool.

7. The medical device of claim 3, wherein the drive mechanism further comprises a rotatable knob configured to rotate the drive shaft and the spool.

8. The medical device of claim 1, further comprising a medical tube connector that is coupled to the opening of the enclosure and removably coupleable to the medical tube to form a closed passageway for fluid communication between the discrete conduit of the interior of the enclosure and the medical tube through the medical tube connector.

9. The medical device of claim 1, further comprising a drainage tube connector that is coupled to the enclosure and removably coupleable to a drainage tube.

10. The medical device of claim 9, wherein a vacuum source is coupled to the drainage tube to provide a vacuum to draw fluid into the drainage tube.

11. The medical device of claim 1, further comprising a clearance member coupled to a distal end of the elongated guide member.

12. The medical device of claim 1, wherein the control system comprises a sensor configured to detect an operating parameter.

13. The medical device of claim 12, wherein the operating parameter is a degree of translation of the elongated guide member.

14. The medical device of claim 12, wherein the operating parameter is a length of the medical tube.

15. The medical device of claim 12, wherein the operating parameter is a torque in the drive mechanism.

16. The medical device of claim 12, wherein the operating parameter is a pressure in the medical tube.

17. The medical device of claim 12, wherein the operating parameter is a pressure in a drainage tube that is coupled to the enclosure.

18. The medical device of claim 12, further comprising an alarm configured to activate based on the operating parameter detected by the sensor.

19. The medical device of claim 12, wherein the control system is further configured to automatically control the operation of the drive mechanism based on the operating parameter detected by the sensor.

20. The medical device of claim 1, further comprising a seal member configured to inhibit fluid communication between the interior of the enclosure and the exterior of the enclosure.

21. The medical device of claim 1, said opening being aligned so that said elongated guide member follows a substantially tangential path relative to the spool, from said spool out of the enclosure via said opening.

22. A medical device for clearing obstructions from a medical tube, the medical device comprising:
    an enclosure defining (i) an interior comprising a sterile field and having a discrete spool chamber isolated from a remainder of the interior, (ii) an exterior, and (iii) an opening for providing access to the interior;
    a drive mechanism;
    a rotatable spool located within the discrete spool chamber;
    a control system configured to automatically control operation of the drive mechanism; and
    an elongated guide member at least partially wound on the rotatable spool;
    the drive mechanism being configured to (i) advance the elongated guide member out of the enclosure through the opening without compromising the sterile field and (ii) withdraw the elongated guide member into the enclosure through the opening without compromising the sterile field,
    said drive mechanism comprising a magnetic spool element coupled to the rotatable spool and a magnetic drive element provided outside of the enclosure and magnetically coupled to the magnetic spool element, wherein movement of the magnetic drive element is configured to cause rotation of the rotatable spool via said magnetic coupling.

* * * * *